United States Patent
Bolton et al.

(10) Patent No.: US 6,306,959 B1
(45) Date of Patent: Oct. 23, 2001

(54) RAPID PURIFICATION BY POLYMER SUPPORTED QUENCH

(75) Inventors: Gary L. Bolton, Ann Arbor; Richard J. Booth, Ypsilanti; Mark W. Creswell, Chelsea; John C. Hodges, Ann Arbor; Joseph S. Warmus, Ann Arbor; Michael W. Wilson, Ann Arbor, all of MI (US)

(73) Assignee: Warner Lambert Company, Ann Arbor, MI (US)

( * ) Notice: Subject to any disclaimer, the term of this patent is extended or adjusted under 35 U.S.C. 154(b) by 0 days.

(21) Appl. No.: 09/171,258

(22) PCT Filed: Apr. 28, 1997

(86) PCT No.: PCT/US97/07099

§ 371 Date: Oct. 15, 1998

§ 102(e) Date: Oct. 15, 1998

(87) PCT Pub. No.: WO97/42230

PCT Pub. Date: Nov. 13, 1997

Related U.S. Application Data

(60) Provisional application No. 60/017,422, filed on May 3, 1996.

(51) Int. Cl.⁷ .................................................. C08G 63/48
(52) U.S. Cl. .................... 525/54.1; 530/810; 530/815; 530/816; 530/817
(58) Field of Search .......................... 525/54.1; 530/810, 530/815, 816, 817

(56) References Cited

U.S. PATENT DOCUMENTS

| | | |
|---|---|---|
| 3,917,469 | 11/1975 | Cotter et al. |
| 4,038,469 | 7/1977 | Walker et al. |
| 4,076,913 | 2/1978 | Walker et al. |
| 4,215,219 | 7/1980 | Patchornik et al. |
| 5,049,656 | 9/1991 | Lewis et al. |
| 5,055,197 | 10/1991 | Albright et al. |
| 5,071,565 | 12/1991 | Fritz et al. |
| 5,230,806 | 7/1993 | Fritz et al. |
| 5,288,514 | 2/1994 | Ellman. |
| 5,391,298 | 2/1995 | Pieper et al. |
| 5,403,489 | 4/1995 | Hagen et al. |
| 5,547,760 | 8/1996 | Tarbet et al. |
| 5,618,438 | 4/1997 | Fritz et al. |
| 5,696,236 | 12/1997 | Omar et al. |
| 5,700,916 | 12/1997 | Kahne et al. |
| 5,767,238 | 6/1998 | Caporale. |

FOREIGN PATENT DOCUMENTS

| | | |
|---|---|---|
| 25 04 397 | 8/1975 | (DE). |
| 0 523 480 A1 | 1/1993 | (EP). |
| 02204474 | 11/1997 | (JP). |
| WO 93/09668 | 5/1993 | (WO). |

OTHER PUBLICATIONS

"Kinetic Studies of the Liquid Phase Peptide Synthesis", E. Bayer et al, Journal of the American Chemical Society, 96:23, pp. 7333–7336, Nov. 13, 1974.

"HELP (High Efficiency Liquid Phase) new oligonucleotide synthesis on soluble polymeric support", Gian Maria Bonora, et al, 1990 Oxford University Press, Nucleic Acids Research, vol. 18, No. 11, pp. 3155–3159.

"Use of peptide synthesis to probe viral antigens for epitopes to a resolution of a single amino acid", H. Mario Geysen, et al, Proc. Natl. Acad. Sci. USA, pp. 3998–4002, (1984).

"Simultaneous Multiple Peptide Synthesis Under Continuous Flow Conditions On Cellulose Paper Discs As Segmental Solid Supports", Ronald Frank, et al, Tetrahedron, vol. 44, No. 19, pp. 6031–6040 (1988).

"Synthesis Of Defined Peptide–Oligonucleotide Hybrids Containing A Nuclear Transport Signal Sequence", Ramon Eritza, et al, Tetrahedron, vol. 47, No. 24, pp. 4113–4120 (1991).

"Simultaneous multiple synthesis of peptide–carrier conjugates", N. Joe Maeji, et al, Journal of Immunological Methods, 146, pp. 83–90 (1992).

"Facile Preparation Of 3 Oligonucleotide–Peptide Conjugates", Carl D. Juby, et al, Tetrahedron Letters, vol. 32, No. 7, pp. 879–882 (1991).

"Generation and use of synthetic peptide combinational libraries for basic research and drug discovery", Richard A. Houghten, et al, Nature, vol. 354, pp. 84–86, Nov. 7, 1991.

"Peptides on phage: A vast library of peptides for identifying ligands", Steven E. Cwirla, et al, Proc. Natl. Acad. Sci. USA, vol. 87, pp. 6378–6382, Aug. 1990.

"The Use Of Insoluble Polymer Supports in General Organic Synthesis", Clifford C. Leznoff, Accounts of Chemical Research, vol. 11, pp. 327–333 (1978).

(List continued on next page.)

*Primary Examiner*—Nathan M. Nutter
(74) *Attorney, Agent, or Firm*—Reising, Ethington, Barnes, Kisselle, Learman & McCulloch, P.C.; Francis J. Tinney

(57) ABSTRACT

Novel polymer-supported quenching reagents of Formula (I): P-L-Q, wherein P is a polymer of low chemical reactivity which is soluble or insoluble; Q is one or more quenching reagents, or an acid or base addition salts thereof, that are capable of selective covalent reaction with unwanted byproducts, or excess reagents; and L is one or more chemically robust linkers that join P and Q; are described, as well as methods for their preparation and methods for their use in the rapid purification of synthetic intermediates and products in organic synthesis, combinatorial chemistry and automated organic synthesis.

13 Claims, No Drawings

OTHER PUBLICATIONS

"The monoblocking of symmetrical diketones on insoluble polymer supports", Zhang–Huang Xu, et al, Can. J. Chem, vol. 61, pp. 1405–1409, (1983).

"Sequential Multistep Reactions Catalyzed by Polymer–Anchored Homogeneous Catalysts", Charles U. Pittman, Jr., et al, Journal of the American Chemical Society, vol. 97, No. 7, Apr. 2, 1975.

"A Polymer–Bound Bidentate–Phosphine–Palladium Comples as a Catalysts in the Heck Arylation", Pei–Wei Wang, et al, J. Org. Chem., vol. 59, No. 18 pp. 5358–5364, (1994).

"Silica Gel Functionalized With Amino Groups As A New Catalyst For Knoevenagel Condensation Under Heterogeneous Catalysis Conditions", Enrico Angeletti, et al, Tetrahedron Letters, vol. 29, No. 18, pp. 2261–2264 (1988).

"Generation and use of Synthetic Peptide Combinatorial Libraries for basic research and drug discovery", Richard A. Houghten, Nature, vol. 354, pp. 84–86, Nov. 7, 1991.

"Separation Of Cis Diols From Isomeric Cis–Trans Mixtures By Selective Coupling To A Regenerable Solid Support", Elizabeth Seymour, et al, Tetrahedron Letters, No. 41, pp. 3669–3672 (1976).

"Syntheses And Separations Using Functional Polymers", D. C. Sherrington, et al, John Wiley & Sons Ltd, pp. 108–113 (1988).

"Use of Solid Supported Nucleophiles and Electrophiles for the Purification of Non–Peptide Small Molecule Libraries", Tetrahedron Letters, vol. 37, No. 40, pp. 7193–7196 (1996).

"Piperazino–Functionalized Silica Gel as a Deblocking-–Scavenging Agent for the 9–Fluorenylmethyloxycarbonyl Amino–Protecting Group", Louis A. Carpino, et al, J. Org. Chem. vol. 48, No. 5, pp. 666–669 (1983).

"Discovery Of Antirhinoviral Leads By Screening A Combinatorial Library Of Ureas Prepared Using Covalent Scavengers", Stephen W. Kaldor, Bioorganic & Medicinal Chemistry Letters, vol. 6, No. 24, pp. 3041–3044 (1996).

Postcondensation Modifications of Ugi Four–Component Condensation Products: 1–Isocyanocyclohexene as a Convertible Isocyanide. Mechanism of Conversion, Synthesis of Diverse Structues, and Demonstration of Resin Capture, Thomas A. Keating, J. Am. Chem. Soc., vol. 118, No. 11, pp. 2574–2583 (1996).

"Preparation of a Polymer–supported Diol and Its Use in isolating Aldehydes and Ketones from Mixtures and as a Protecting Group for Aldehydes and Ketones", Philip Hodge, et al, J. Chem. Soc. Perkin Trans. I, pp. 2319–2323 (1983).

"Diethylamine Addition To Natural Sesquiterpenic β–Exomethylene–γ–Lactones And Its Use For Chemical Transformations Of These Compounds", Jurai Harmatha, et al, Collection Czechoslovak Chem. Commun, vol. 47, pp. 2779–2785 (1982).

A soluble Polymer Approach to the "Fishing Out" Principle: Synthesis and Purification of β–Amino Alcholos, Manabu Hori Kim D. Janda, J. Org. Chem., vol. 63, No. 3, pp. 889–894 (1998).

"Preparation and Use of Synthetic Cell Culture Surfaces", Rampyari H. Raja, et al, The Journal Of Biological Chemistry, vol. 261, vol. 18, pp. 8505–8513 (1986).

JP Polym Sci., Polym. Chem. Ed (Abstract) (1967), 5(6), 1245–65.

Nature, Friday May 5, 1972, vol. 237, No. 5349, pp. 512–513 (1972).

Latv. PSR Zinat. Akad. Vestis, Kim. Ser. (1986), (5), 618–24.

Scientia Sinica, Authors Anonymous, (Abstract) 18(6): 745:68, 1975 Nov.–Dec.

"Automatically Programmed Synthesizer For The Liquid Phase Synthesis", E. Bayer, et al, Peptides: Chemistry, Structure, Biology, Synthetic Studies, pp. 425–432, 1975.

"Light–Directed, Spatially Addressable Parallel Chemical Synthesis", Stephen P. A. Fodor, et al, Research Article, Science, vol. 25, pp. 767–773, Feb. 1991.

"Use Of Polymeric Nucelophiles For The Selective Binding And Removal Of a–Methylene–Y–Butyrolactone Allergens From Complex Mixtures", Annie Cheminat, et al, Tetrahedron Letters, vol. 21, pp. 617–620, 1980.

RAPID PURIFICATION BY POLYMER SUPPORTED QUENCH

CROSS-REFERENCE TO RELATED CASES

Applicant relies upon the provisional patent application filed on May 3, 1996 having Ser. No. 60/017,422. This application is filed under the provision of 35 U.S.C. 371 claiming the International filing date of Apr. 28, 1997.

BACKGROUND OF THE INVENTION

The present invention relates to novel polymer-supported quenching reagents, to methods for their preparation, and to methods for their use in the rapid purification of synthetic intermediates and products in the practice of organic synthesis, combinatorial chemistry, and automated organic synthesis.

Combinatorial chemistry and automated organic synthesis have proven to be highly effective means for the generation of multiplicities of novel molecules known as libraries. As the size of such a library grows, so does the likelihood that it will contain individual molecules with useful biological activities which may be employed in the treatment of human, animal, and plant diseases. Research organizations that can prepare and screen a large number of diverse compounds efficiently, have an increased likelihood of discovering and optimizing new products. For recent reviews in the use of combinatorial chemistry in pharmaceutical discovery see Gallop M. A., et al., *J. Med. Chem.*, 1994;37:1233 and Gordon E. M., et al., ibid., 1994;37:1385.

In the practice of organic synthesis, the most time consuming element is typically the purification of the desired product following each synthetic transformation. Traditionally, automated organic synthesis and combinatorial chemistry have relied on a number of methods to reduce the amount of time and effort devoted to purification. Such methods include water soluble reagents, polymer-supported reagents, and polymer-supported synthesis. Water soluble reagents and byproducts derived therefrom have the advantage of being easily removed by partitioning the crude reaction mixture between water (which dissolves the reagent and associated byproducts) and an organic solvent (which dissolves the desired product). Separation of the organic layer gives a purified form of the product relative to the crude reaction mixture. An example of a water soluble reagent is N-ethyl-N'-dimethylaminopropylcarbodiimide (EDC). EDC is a reagent that is used in the coupling of carboxylic acids and amines to form amide bonds. EDC and the corresponding urea produced during the course of the reaction (N-ethyl-N'-dimethylaminopropylurea) are both soluble in water at low pH and can thus be washed away into an acidic water layer. The use of EDC greatly simplifies purification of the amide product relative to other carbodiimides such as N,N'-dicyclohexylcarbodiimide (DCC) which are not water soluble. Polymer-supported reagents and byproducts derived therefrom are likewise easily separated by filtration of the polymeric materials from a crude reaction mixture. An example of a polymer-supported reagent is poly(styrene-divinylbenzene)-supported triphenylphosphine which may be used in Wittig olefination reactions. The byproduct of this transformation, polymer-supported triphenylphosphine oxide, is easily removed by filtration which simplifies purification greatly compared to the solution phase reagent. The use of triphenylphosphine in solution phase Wittig reactions gives triphenylphosphine oxide as a byproduct which is difficult to completely remove except by time consuming chromatography or repeated crystallization. Polymer-supported synthesis minimizes time spent on purifications by attaching a starting material to a polymer. Subsequent synthetic transformations are carried out in such a manner that desired reactions are driven to completion on the polymer-supported material and excess reagents and byproducts in solution are subsequently removed by filtering the polymer and rinsing with solvent (s). At the end of the synthesis, the desired product is chemically cleaved from the polymer. The resulting product is typically obtained in greater purity than would be possible if all of the steps were carried out in solution with no chromatography or crystallization of synthetic intermediates. Purification in a multistep synthesis is thus largely reduced to a number of filtrations, although a single purification of the final product by conventional means is often necessary to remove byproducts resulting from the resin cleavage step. Thus, water soluble reagents, polymer-supported reagents, and polymer-supported synthesis each provide increased efficiency reducing purification to mechanically simple liquid-liquid and liquid-solid separation methods which are easy to automate.

The increased simplicity and efficiency which allow automation of organic synthesis using the methods described above comes at the price of increased reagent cost and/or substantial synthesis development time. Water soluble reagents and polymer-supported reagents must be customized for each type of synthetic transformation. The time necessary to optimize a particular reagent significantly increases its cost. Consequently, EDC is more expensive than DCC and polystyrene-supported triphenylphosphine is more expensive than triphenylphosphine. Polymer-supported syntheses traditionally require longer development time than solution phase due to the limitations imposed by the method. One must choose the optimum polymer, develop a linking strategy which can be reversed at the end of the synthesis and find successful conditions for each reaction without many of the conventional spectral and chromatographic analysis tools that are available to solution phase synthesis. Thus, at the current state of the art, much of the time/cost saved by increasing the efficiency of purifications via the above methods is lost to increased reagent costs and/or synthetic development time.

Polymer-supported reagents have been extensively reviewed in the literature. The following citation is representative of the current state of this art: Sherrington D. C., *Chem. Ind.*, (London) 1991;1:15–19.

Solid-supported synthesis has been extensively reviewed in the literature. The following two citations are representative of the current state of this art: Früchtel J. S. and Jung G., *Angew. Chem. Int. Ed. Engl.*, 1996;35:17–42, Thompson L. A. and Ellman J. A., *Chem. Rev.*, 1996;96:555–600.

A purification process known as covalent chromatography has been described in the scientific literature. Using covalent chromatography a desired material is isolated from a complex mixture by selective reaction with a polymeric reagent, followed by filtration, and rinsing. The desired material is then liberated from the polymer by a chemical cleavage. Typically this process is applied to proteins and other macromolecules as a way of isolating them from complex mixtures of cellular components. This technique has also been applied in the separation of low molecular weight allergens from plant oils as described by Cheminat A., et al., in *Tetr. Lett.*, 1990;617–619. Covalent chromatography differs from the instant invention in that the polymeric materials used must be both capable of covalently reacting with a desired material in a solution containing impurities and capable of subsequent cleavage of said covalent bond during the retrieval of the desired material. Polymer-supported quench methods of the present invention rely on chemically robust and ideally irreversible attachment of undesired materials that are found in the crude product of an organic reaction to a polymeric support, leaving the desired product in solution.

Polymeric reagents have been employed during the course of a reaction to enhance yield of the desired product by minimizing side reactions as described by Rubenstein M. and Patchornik A., *Tetr. Lett.*, 1975;1445–8, but this use of a polymeric reagent does not eliminate the need for conventional purification of the desired product.

Polymeric reagents which selectively remove metal ions from solutions by chelation have been described but this use of a polymeric reagent in purification does not involve formation of covalent bonds. For a review of the current state of this art see Alexandratos S. D. and Crick D. W., *Ind. Eng. Chem. Res.*, 1996;35:635–44.

The synthesis of dendritic polyamides on polymeric supports has been described by Ulrich K. E., et al., *Polymer Bul.*, 1991;25:551–8. As synthetic intermediates of the synthesis, polymer-supported dendritic polyamines are described which, by virtue of the fact that they contain an easily cleaved linker, are structurally distinct from those of the present invention which contain chemically robust linkers.

The aforementioned references do not describe or suggest the polymer-supported quench reagents disclosed herein, nor do they teach methods of preparation of polymer-supported quench reagents disclosed herein, nor do they teach the rapid purification utility of polymer-supported quench in the practice of automated organic synthesis and combinatorial chemistry as described in the present invention.

Thus, we have surprisingly and unexpectedly found that one or more polymer-supported reagents can be added at the conclusion of an organic reaction to covalently react with excess reagents and/or unwanted byproducts. The polymer bound impurities are then easily removed by conventional solid-liquid phase separation techniques leaving a solution of the desired synthetic intermediate or product which is enhanced in purity relative to the crude reaction mixture. Purification by polymer-supported quench is mechanically simple and rapid compared to conventional means of purification such as column chromatography, distillation or crystallization. This means of purification is readily applied to large variety of organic reactions and is amenable to both manual and automated organic synthesis environments. Hence, it is of tremendous value in the preparation of large libraries of organic molecules by automated parallel synthesis and by automated or manual conbinatorial synthesis.

SUMMARY OF THE INVENTION

Accordingly a first aspect of the present invention is a compound of Formula I,

P-L-Q                                                            I wherein

P is a polymer of low chemical reactivity which is soluble or insoluble;

Q is one or more quenching reagents, or an acid or base addition salt thereof, that are capable of selective covalent reaction with unwanted byproducts, or excess reagents; and L is one or more chemically robust linkers that join P and Q;

with the proviso that a compound of Formula I is not Merrifield resin (also known as chloromethyl-poly(styrene-divinylbenzene); benzylamine resin (also known as aminomethyl-poly(styrene-divinylbenzene)); benzyhdrylamine resin (also known as BHA resin); 4-methyl-benzhydrylamine resin (also known as MBHA resin); benzylalcohol resin (also known as hydroxymethyl-poly(styrene-divinylbenzene)); Wang resin (also known as p-benzyloxy-benzylalcohol resin); aldehyde resin (also known as formyl-poly(styrene-divinylbenzene); TentaGel® hydroxy; amino and thiol resins, benzylthiol resin (also known as thiomethyl-poly(styrene-divinylbenzene); polymer diazomethylene (also known as polymer-supported diphenyl-diazomethane); nor poly(ethyleneglycol).

A second aspect of the present invention is a method for enhancing the purity of a desired compound which comprises:

Step (a) treating a crude reaction product which contains at least one desired compound, unreacted starting materials and/or byproducts with at least one polymer-supported quenching reagent of Formula I,

P-L-Q                                                            I wherein

P is a polymer of low chemical reactivity which is soluble or insoluble;

Q is one or more quenching reagents, or an acid or base addition salt thereof, that are capable of selective covalent reaction with unwanted byproducts, or excess reagents; and L is one or more chemically robust linkers that join P and Q.

Step (b) allowing the polymer-supported quenching reagent to covalently react with unreacted starting materials and/or byproducts to afford a derivatized reagent of Formula II,

P-L-Q-X                                                          I wherein

X is unreacted starting material and/or byproduct and P, L, and Q are as defined above; and Step (c) separation of the reagents of Formula I and Formula II from the solution and removal of solvent to afford a compound of enhanced purity.

A third aspect of the present invention is a process of preparing a compound of Formula I,

P-L-Q                                                            I wherein

P is a polymer of low chemical reactivity which is soluble or insoluble;

Q is one or more quenching reagents, or an acid or base addition salt thereof, that are capable of selective covalent reaction with unwanted byproducts, or excess reagents; and L is one or more chemically robust linkers that join P and Q;

with the proviso that a compound of Formula I is not Merrifield resin (also known as chloromethyl-poly(styrene-divinylbenzene); benzylamine resin (also known as aminomethyl-poly(styrene-divinylbenzene)); benzyhdrylamine resin (also known as BHA resin);

4-methylbenzhydrylamine resin (also known as MBHA resin); benzylalcohol resin (also known as hydroxymethyl-poly(styrene-divinylbenzene)); Wang resin (also known as p-benzyloxybenzylalcohol resin); aldehyde resin (also known as formyl-poly(styrene-divinylbenzene); TentaGel® hydroxy; amino and thiol resins; benzylthiol resin (also known as thiomethyl-poly(styrene-divinylbenzene); polymer diazomethylene (also known as polymer-supported diphenyl-diazomethane); nor poly(ethyleneglycol), which comprises conversion of a polymeric starting material to a compound of Formula I in one to four synthetic steps, rinsing thoroughly with one or more solvents after each synthetic step.

DETAILED DESCRIPTION OF THE INVENTION

The following Table 1 provides a list of definitions and abbreviations used in the present invention.

TABLE 1

DEFINITIONS AND ABBREVIATIONS

| Term | Definition |
| --- | --- |
| Acid addition salt | A salt derived from inorganic acids such as, for example, hydrochloric, nitric, phosphoric, sulfuric, hydrobromic, hydriodic, phosphorous, and the like, as well as from water soluble organic acids such as, for example, aliphatic mono- and dicarboxylic acids, phenyl-substituted alkanoic acids, hydroxy alkanoic acids, aromatic acids, aliphatic, and aromatic sulfonic acids and the like. |
| Base addition salt | A salt derived from inorganic metals such as, for example, sodium, potassium, magnesium, calcium, and the like as well as from water soluble organic amines such as, for example, N-methylmorpholine, diethanolamine, ethylenediamine, procaine, and the like. |
| Byproduct | An undesirable product of a reaction which comprises at least five mole percent of the crude product. Isomers, enantiomers and diastereomers of the desired product are not considered to be byproducts within the scope of this invention. |
| Chemically robust | Not cleaved by a wide variety of reagents used in the art of organic synthesis. |
| Crude reaction product | The result of a chemical reaction before any purification. Synonymous with crude product and crude reaction mixture. |
| Dendritic molecule | A subset of polyfunctional molecules which have two or more equivalent arm-like structures with functional groups at the ends emanating from a central core structure. For example, tris (2-aminoethyl)-amine, ethylenediaminetetraacetic acid, tris (hydroxymethyl) aminomethane, and 1,3,5-benzenetricarboxylic acid are dendritic molecules. |
| Enhancing purity | A) For a single desired compound, enhancing purity means the process of removing excess or unreacted starting reagents to the limit of detection by TLC or by NMR spectroscopy and/or reducing the content of any single byproduct to less than ten molar percent, exclusive of solvents B) For a combinatorial mixture of desired compounds: The process of removing excess or unreacted starting reagents and or reducing the content of a byproduct using a procedure that has been validated on crude reaction products of analogous single compounds. |
| Insoluble polymer | A polymeric compound which by virtue of its structure and high molecular weight is incapable of dissolving in organic and aqueous solvents and mixtures thereof. |
| Polyfunctional molecule | A compound which contains two or more functional groups attached to a carbon framework or interspersed with more than one carbon framework. For example 2,6-diamino-hexanoic acid, 1,8-diamino-3,6-diazaoctane, and 2,6-diisocyanatohexane are polyfunctional molecules. |
| Quenching reagent | A molecule that covalently combines with a reactant to make it less reactive or a molecule that covalently combines with a byproduct. |
| Resin | A synonym for an insoluble polymer. |
| Resin swelling solvent | A solvent which penetrates pores of an insoluble polymer and causes it to increase in volume. |
| Soluble polymer | A polymeric compound which by virtue of its structure and low molecular weight is able to dissolve in selected solvents. |

| Abbreviation | |
| --- | --- |
| | Structural Group |
| Boc | tertiary Butyloxycarbonyl |
| Fmoc | 9-Fluorenylmethyloxycarbonyl |
| Ph | Phenyl |
| | Solvents and Reagents |
| AcOH (HOAc) | Acetic acid |
| $Ac_2O$ | Acetic acid anhydride |
| BuLi (nBuLi) | n-Butyllithium |
| $Ca_2CO_3$ | Cesium carbonate |
| CDI | N,N'-Carbonyldiimidazole |
| $CF_3SO_2H$ | Trifluoromethanesulfonic acid |
| DBU | 1,8-Diazabicyclo[5.4.0]undec-7-ene |
| DCM | Dichloromethane |
| DCC | N,N'-Dicyclohexylcarbodiimide |
| DCU | N,N'-Dicyclohexylurea |
| DIC | N,N'-Diisopropylcarbodiimide |
| DIEA ($iPr_2NEt$) | N,N-Diisopropylethylamine |
| DMA | N,N-Dimethylacetamide |
| DMAP | 4-Dimethylaminopyridine |
| DMF | N,N-Dimethylformamide |
| DTT | Dithiothreitol |
| EDC (EDAC) | N-Ethyl-N'-Dimethylamino propycarbodiimide |
| EtOAc | Ethyl acetate |
| $Et_2O$ | Diethyl ether |
| EtOH | Ethanol |
| HCl | Hydrochloric acid |

-continued

| Abbreviation | |
|---|---|
| HF | Hydrofluoric acid |
| HOBT | 1-Hydroxybenzotriazole |
| iBuOCOCl | Isobutyl chloroformate |
| iPrOH | iso-Propanol |
| (iPrO)$_3$B | Triisopropyl borate |
| KOtBu | Potassium tert butoxide |
| KOAc | Potassium acetate |
| K$_2$CO$_3$ | Potassium carbonate |
| MCPBA | Meta chloroperbenzoic acid |
| MeCN | Acetonitrile |
| MeI | Iodomethane |
| MeOH | Methanol |
| MgSO$_4$ | Magnesium sulfate |
| NaAl(OtBu)$_3$H | Sodium tri tert butoxyaluminum hydride |
| NaBH$_4$ | Sodium borohydride |
| NaCNBH$_3$ | Sodium cyanoborohydride |
| NaIO$_4$ | Sodium metaperiodate |
| NaI | Sodium iodide |
| NaOEt | Sodium ethoxide |
| NaOH | Sodium hydroxide |
| Na$_2$CO$_3$ | Sodium carbonate |
| NH$_2$NH$_2$(N$_2$H$_4$) | Hydrazine |
| NH$_2$OH | Hydroxylamine |
| NMP | N-Methylpyrrolidone |
| PhN(SO$_2$CF$_3$)$_2$ | N-Phenyltrifluoromethane sulfonamide |
| P(Ph)$_3$I$_2$ | Diiodotriphenylphosphorane |
| (Ph$_3$P)$_4$Pd | Tetrakis (triphenylphosphine) - Palladium(O) |
| TEA (Et$_3$N) | Triethylamine |
| TFA | Trifluoroacetic acid |
| THF | Tetrahydrofuran |
| TMEDA | N,N,N',N'Tetramethylethylene diamine |
| TMG | N,N,N'N'-Tetramethylguanidine |
| Analytical Method | |
| HPLC | High performance liquid chromatography |
| IR | Infrared spectroscopy |
| MS(CI) | Mass spectroscopy with chemical ionization |
| NMR | Nuclear magnetic resonance spectroscopy |
| TLC | Thin layer chromatography |
| GC | Gas chromatography |

The first aspect of the instant invention is a compound of Formula I,

P-L-Q    I wherein
P is a polymer of low chemical reactivity including insoluble polymers such as, for example, poly(styrene-divinylbenzene), methacrylic acid/dimethylacrylamide copolymer, poly(styrene-divinylbenzene/poly(ethyleneglycol) copolymer (also known as TentaGel® hydroxy resin) and soluble polymers such as, for example, polystyrene or poly(ethyleneglycol), and the like;
Q is one or more quenching reagents which contain at least one functional group, or an acid or base addition salts thereof, that is capable of selective covalent reaction with unwanted byproducts, or excess reagents such as, for example, primary amine, secondary amine, tertiary amine, isocyanate, isothiocyanate, carboxylic acid, acid chloride, ketone, aldehyde, cyclic imide, cyclic anhydride, hydroxyl, diol, aminoalcohol, thiol, dithiol, aminothiol, thioether, thiourea, chlorosilane, diene, dienophile, dipole, dipolarophile, enolate, enol ether, alkylsulfonate, alkyl halide, aryl halide, arylsulfonate, arylboronic acid, hydrazine, semicarbazide, acyl hydrazide, hydroxylamine, guanidine, and the like; and
L is linker that joins P and Q such as, for example, CH$_2$—CH$_2$, CH=CH, CH—N, CH$_2$—N, CH—O, CH$_2$—O, CH—S, CH$_2$—S, C(=O)N, NC(=O), NC(=O)N, N(C=O)O, OC(=O)N, combinations thereof, and the like. L is chosen so as to be chemically robust to conditions of rapid purification. In other words, it is necessary that the linker functionality is not cleavable during the course of reaction with excess reagents and unwanted byproducts and subsequent removal.

Generic descriptions of preferred polymer-supported quenching reagents are shown in Schemes 1–18. The most preferred reagents and are listed in Table 2.

The second aspect of the present invention is a method for the preparation of novel polymer-supported quenching reagents from known polymers. Polymer-supported quenching reagents are made in one to four synthetic steps from readily available starting materials, such as for example, insoluble polymers and soluble polymers or derivatives thereof which contain convenient linker functionality, and one or more polyfunctional quenching reagents which bear a compatible connecting functionality and one or more functionalities used in the quenching process.

Preferred polymeric starting materials are insoluble resins with less than five percent crosslinking such as, for example, polystyrene resin (also known as poly(styrene-divinylbenzene)), Merrifield resin (also known as chloromethyl-poly(styrene-divinylbenzene)), benzylalcohol resin (also known as hydroxymethyl resin), poly(styrene-divinylbenzene)/poly(ethyleneglycol) grafted copolymer (also known as TentaGel® hydroxy resin or TG hydroxy resin), benzylamine resin (also known as aminomethyl-poly(styrene-divinylbenzene)), benzhydrylamine resin (also known as BHA resin), 4-methylbenzhydrylamine resin (also known as MBHA resin), TentaGel® amino resin (also known as TG amino resin), aldehyde resin (also known as formyl-poly(styrene-divinyl-benzene), acetyl-poly(styrene-divinylbenzene), benzoyl-poly(styrene-divinylbenzene), carboxy-poly(styrene-divinylbenzene) (also known as carboxylic acid resin), benzylthiol resin (also known as thiomethyl-poly(styrene-divinylbenzene), TentaGel® thiol resin (also known as TG thiol resin), bromo-poly(styrene-divinylbenzene) (also known as brominated polystyrene resin), and the like. The preferred polymeric starting materials are well-known to those skilled in the art of solid-phase peptide synthesis or to those skilled in the art of solid-phase organic synthesis. They are commercially available or are known in the scientific literature.

Contrary to polymer-supported synthesis, where one usually limits the substrate loading to less than or equal to 1 mmol substrate/gram polymer, it is desirable that polymer-supported quenching reagents have a high loading of reactive groups which perform the quench. Preferred polymer-supported quenching reagents have greater than or equal to 1 mmol reactive group per gram of polymer. Most preferred quenching reagents have greater than 2 mmol reactive group per gram of polymer. It is still possible to use polymer-supported quenching reagents with less than 1 mmol reactive group per gram of polymer provided that larger quantities of the quenching polymer are used. In this regard, many solid-phase synthesis polymers which are well known to those skilled in the art of solid-phase peptide chemistry or in the art of solid-phase organic synthesis are viable polymer-supported quenching reagents, including but not limited to, Merrifield resin, benzylamine resin, benzhydrylamine resin, 4-methylbenzhydrylamine resin, benzylalcohol resin, Wang resin, aldehyde resin, TentaGel® hydroxy, amino and thiol resins, benzylthiol resin, polymer diazomethylene, poly(ethyleneglycol), and the like.

Preferred solvents used in the chemical transformations of preferred starting polymers which lead to novel polymer-supported quenching reagents include, for example, DMF, DMA, NMP, DCM, dioxane, THF, benzene, and the like. After each chemical transformation, the polymer is washed with successive cycles of solvents which may include but are not limited to DCM, chloroform, DMF, DMA, dioxane, diethyl ether, THF, benzene, toluene, hexanes, cyclohexane, methanol, ethanol, isopropanol, ethylacetate, water, triethylamine, N-methylmorpholine, acetic acid, trifluoroacetic acid, combinations thereof, and the like.

Preferred methods which afford preferred polymer-supported quenching reagents are described in Schemes 1–18. In general, there are two synthetic strategies by which the preferred high loading of quenching functionality on polymeric supports is achieved. In the first strategy, a polymer with existing functionality of greater than 1 mmol per gram of polymer is chemically modified to give a novel polymer-supported quenching reagent which has greater than 1 mmol of quenching functionality per gram of polymer. In the second strategy, polyfunctional or dendritic molecules bearing connecting functional groups and two or more quenching functional groups are attached to polymers with less than 2 mmol of attachment sites per gram of polymer. In this manner, the number of quenching sites is amplified compared to the number of attachment sites. Specific methods which afford selected examples of most preferred polymer-supported quenching reagents are illustrated in Examples 1–18.

The following legend applies to structures in Schemes 1–18, Equations 1.0–5.0, Table 2, and the Examples.

| | Legend |
|---|---|
| (PS) | = insoluble, polystyrene-divinylbenzene |
| (TG) | = insoluble, TentaGel® |
| (P) | = any soluble or insoluble polymer |
| R | = H or $CH_3$ |
| $R^1$ | = H, Ph, or 4-MePh |
| $R^2$ | = Me, Et, iPr, tBu, Ph |
| $R^3$ | = any secondary amine, especially cyclic aliphatic amines |
| $R^4$ | = any primary or secondary amine |
| $R^5$ | = Me, $CF_3$, $C_2F_5$, Ph, 4-MePh, 4-$NO_2$Ph, 4-BrPh, 4-ClPh, 4-FPh, 4-$CF_3$Ph |
| $R^6$ | = $CH_2Ph$, Me, Et, nPr, nBu, $CH_2CH=CH_2$ |
| (L) | = linker |
| X | = O or S |
| Y | = Cl, imidazol-1-yl, 1,2,3-triazol-1-yl or 2-pyridyloxy |

-continued

| | Legend |
|---|---|
| n | = 2 to 8 |
| m | = 3 to 9 |
| p | = 0 to 10 |
| (EWG) | = electron withdrawing group such as $NO_2$, $CO_2Me$, CN, $CF_3$, etc. |
| $M^+$ | = $Li^+$, $Na^+$, $K^+$, $MgBr^+$, $Cs^+$ |

SCHEME 1
Preparations of Polymer-Supported
Quenching Amines from Merrifield Resin

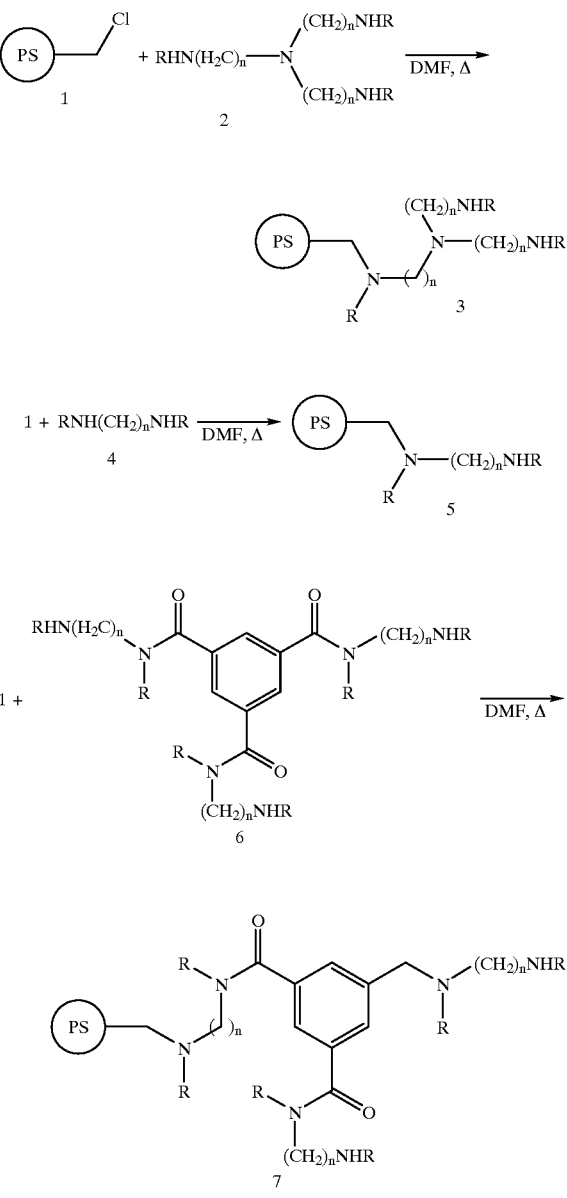

SCHEME 2
Preparations of Polymer-Supported Quenching Amines from Common Amino Resins
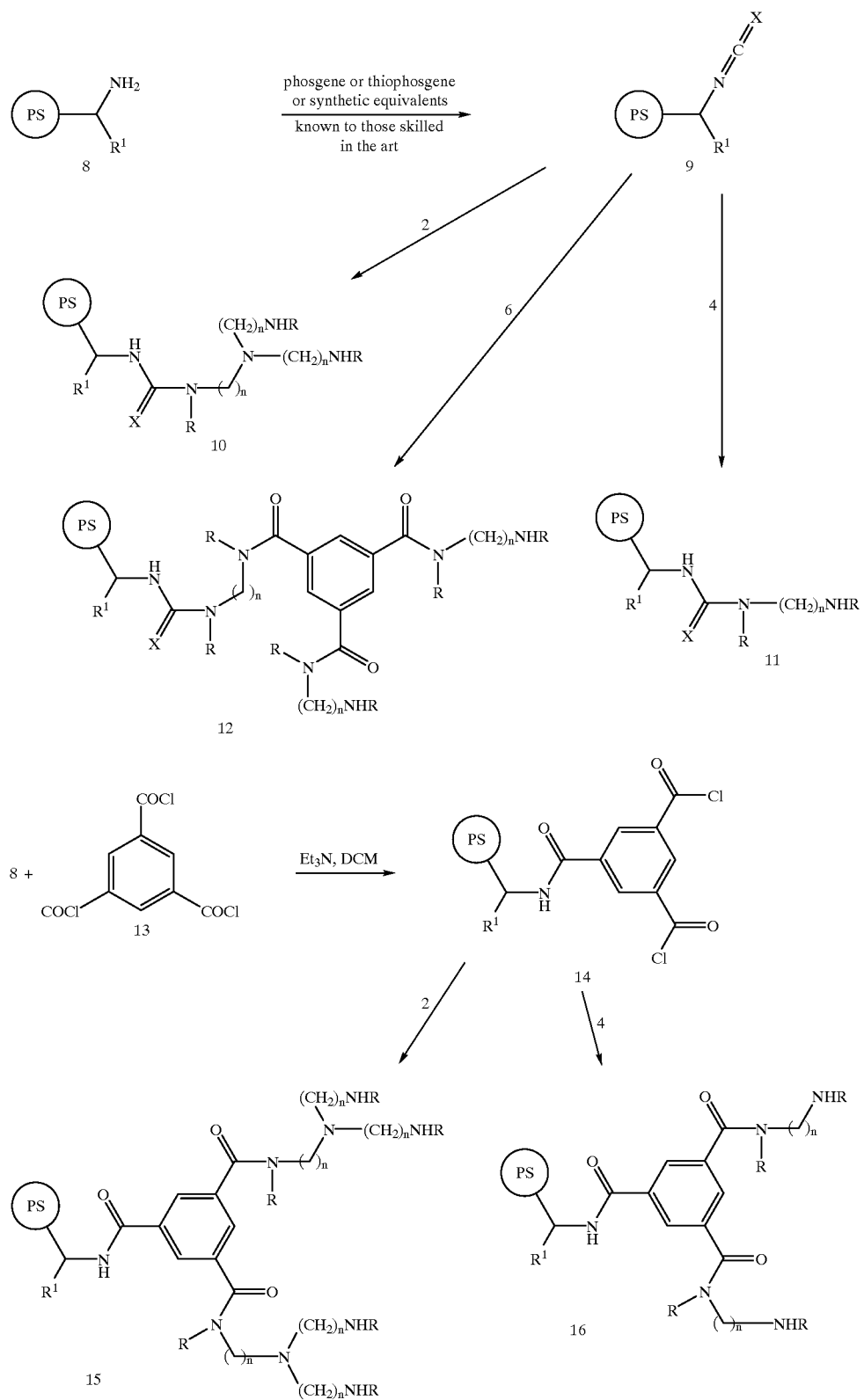

SCHEME 3
Preparations of Polymer-Supported Quenching Amines from Common Hydroxy Resins
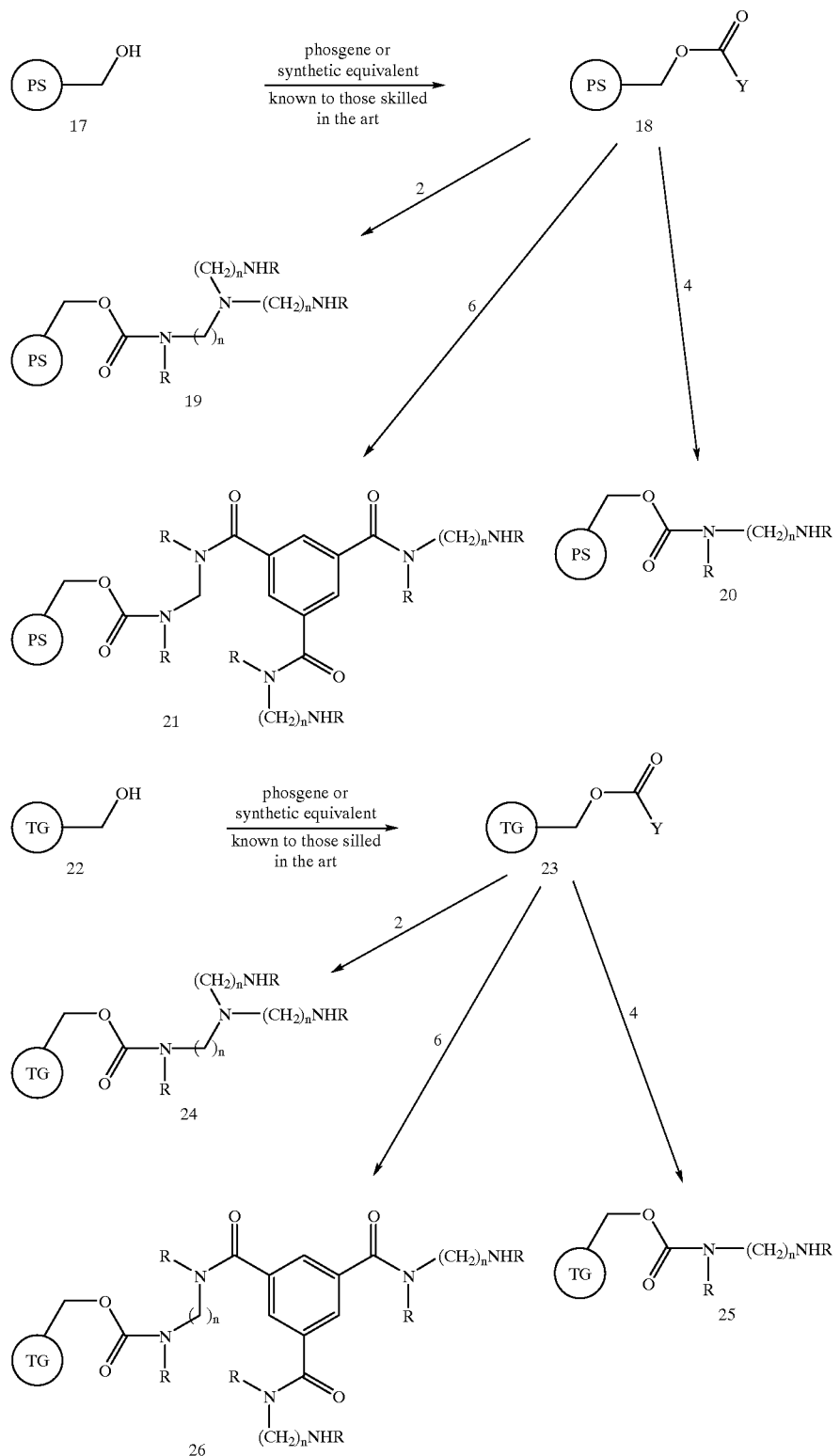

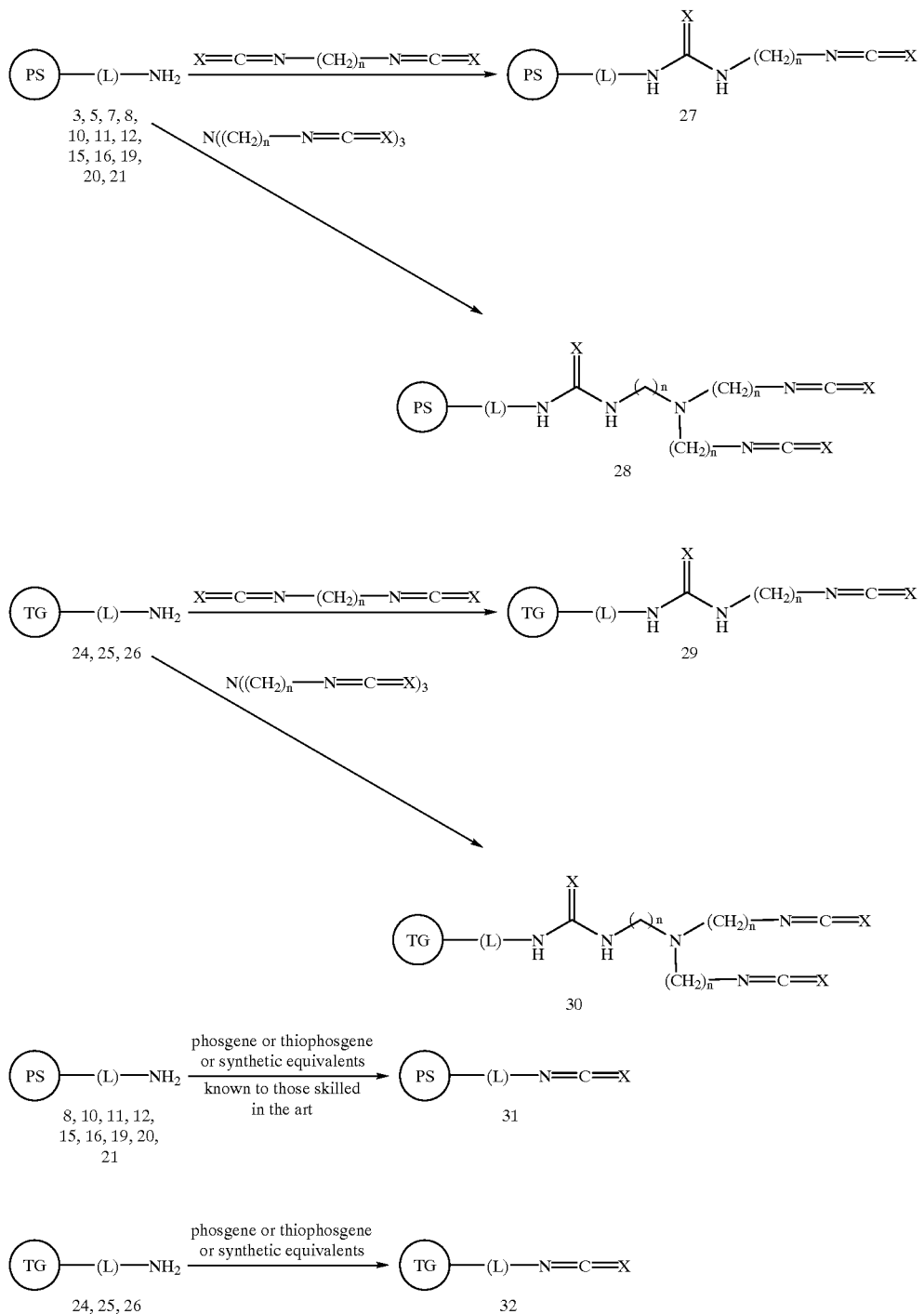

SCHEME 5
Preparations of Polymer-Supported Quenching
Acid Chlorides, Carboxylic Acids, and Aldehydes
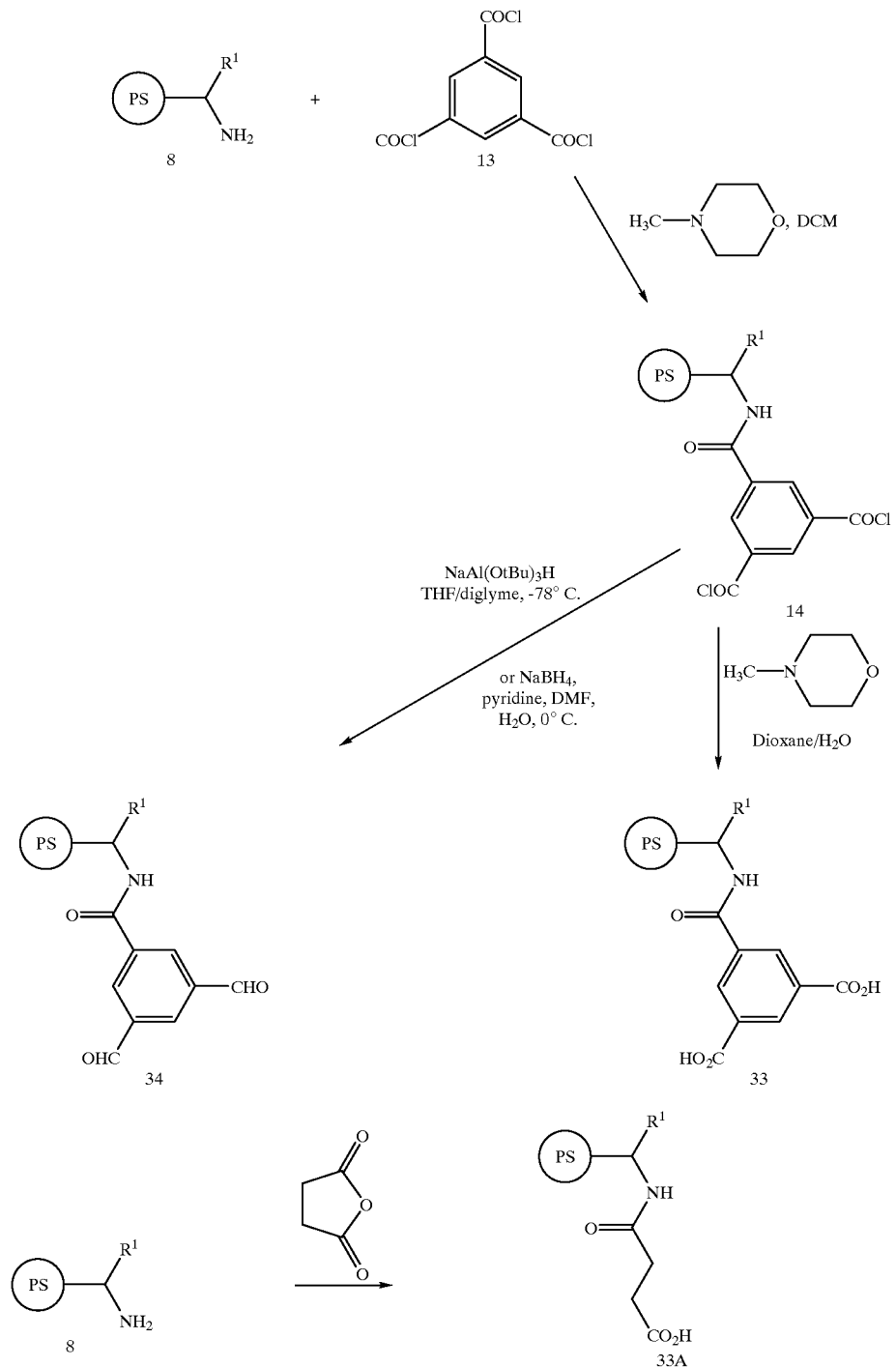

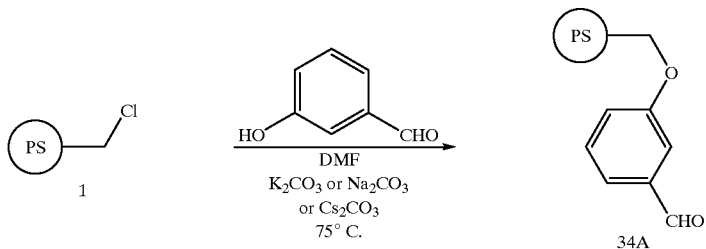
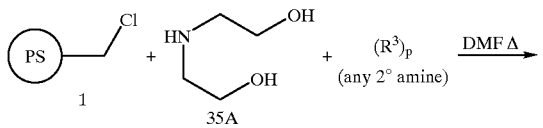
SCHEME 6
Preparations of Polymer-Supported
Quenching Aminoalcohols from Merrifield Resin
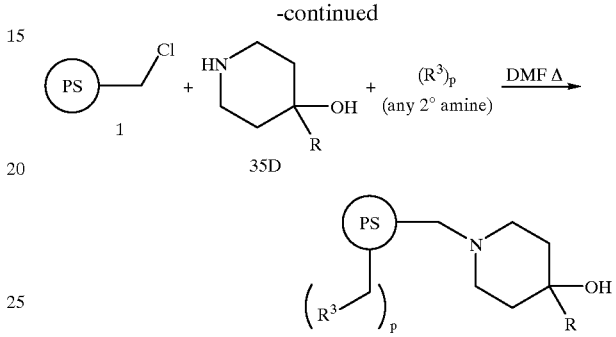
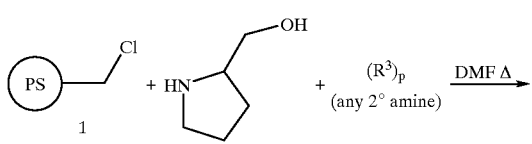
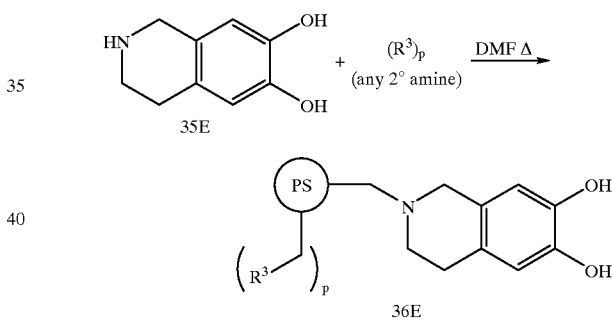
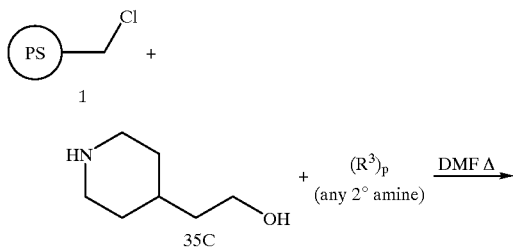
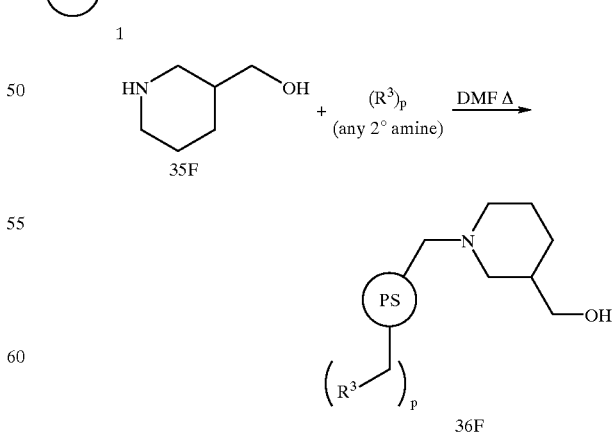

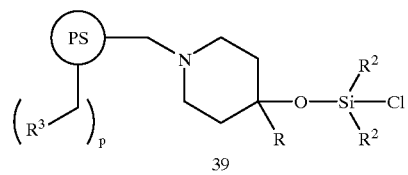
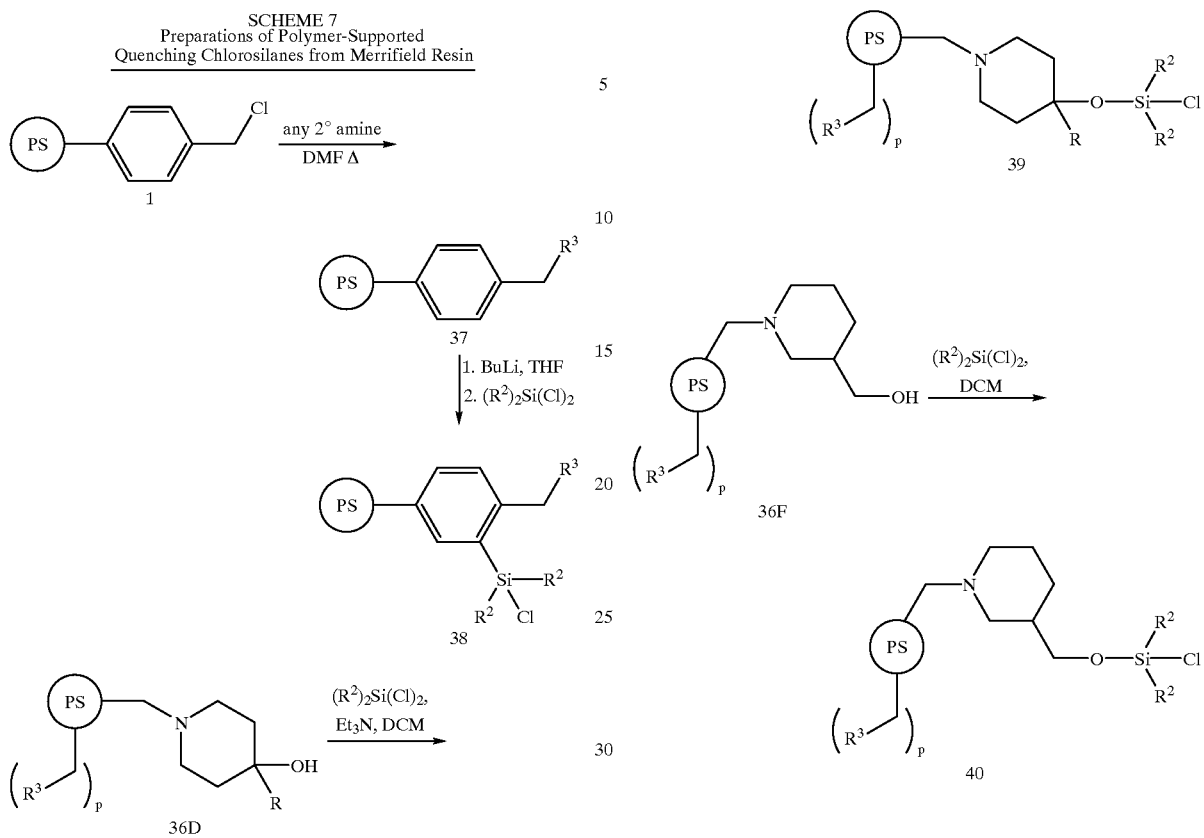

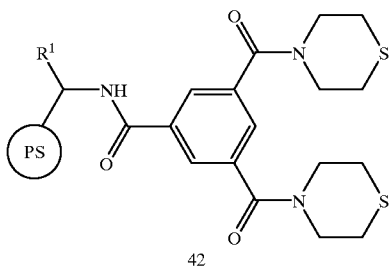
42
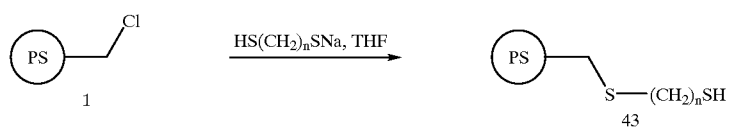
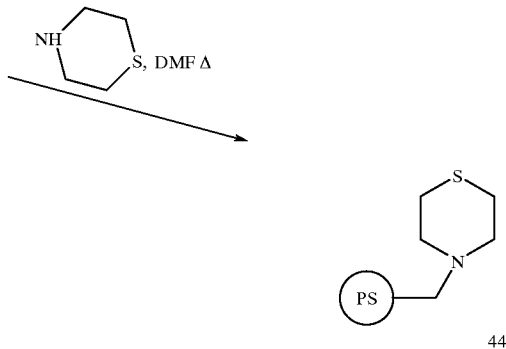
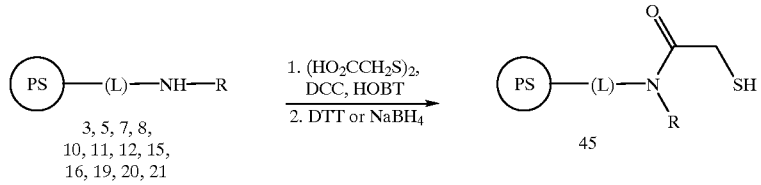
SCHEME 9
Preparations of Polymer-Supported
Quenching Aryl Boronic Acids
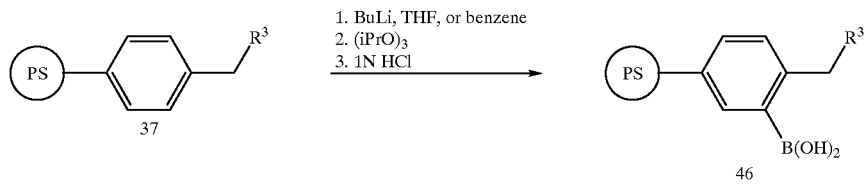
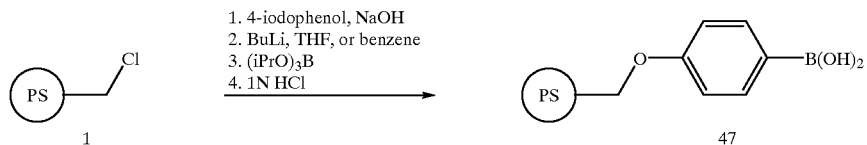
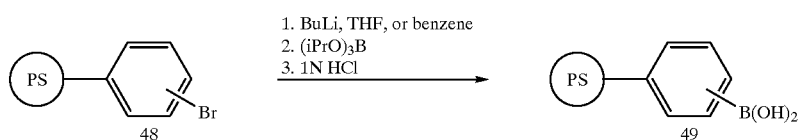

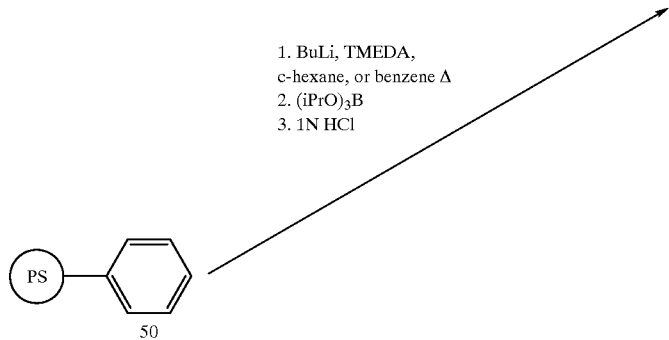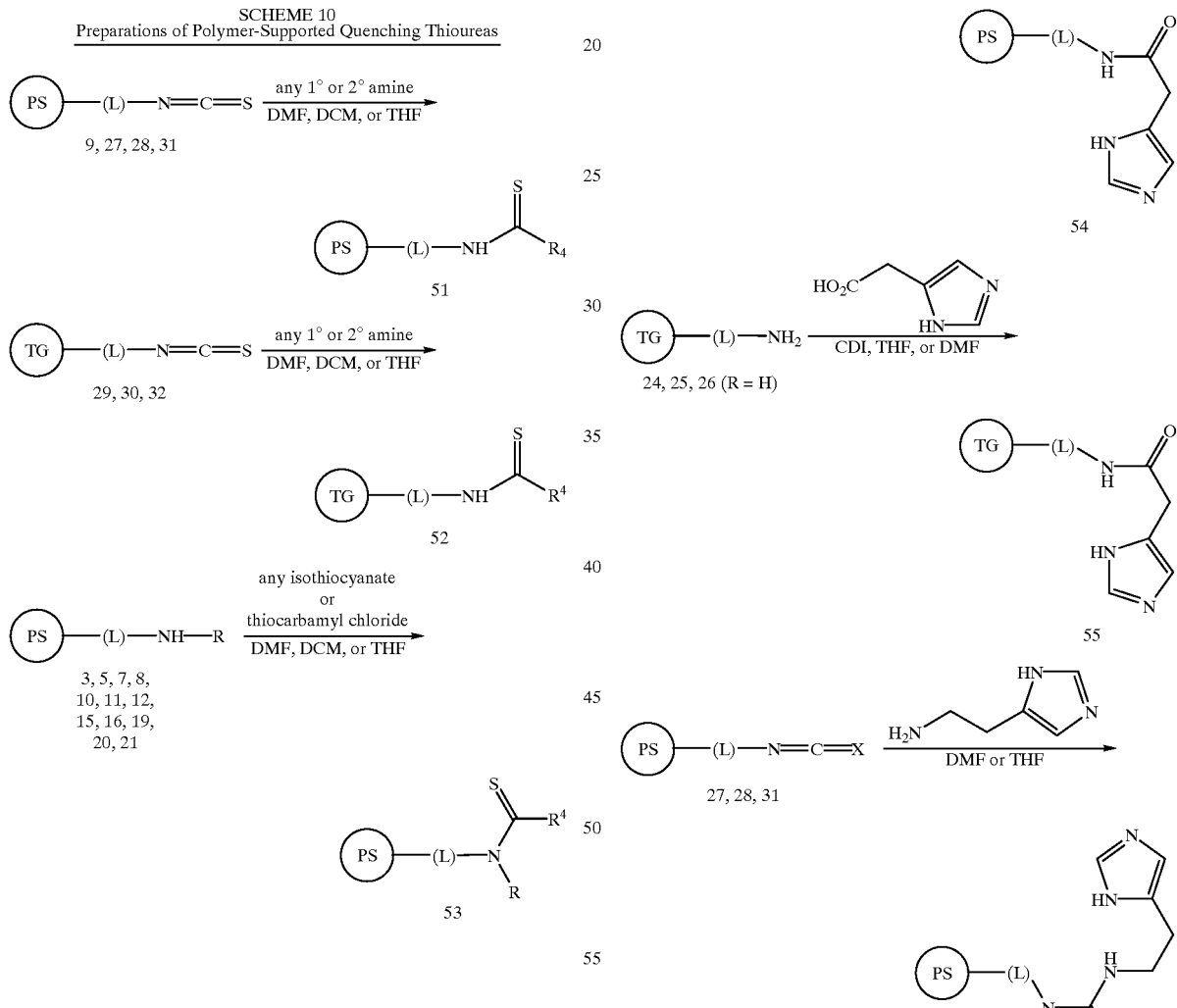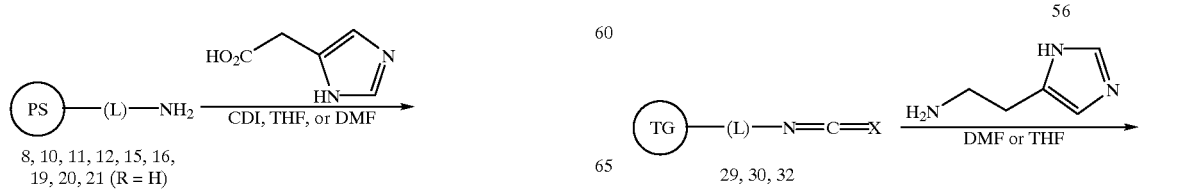

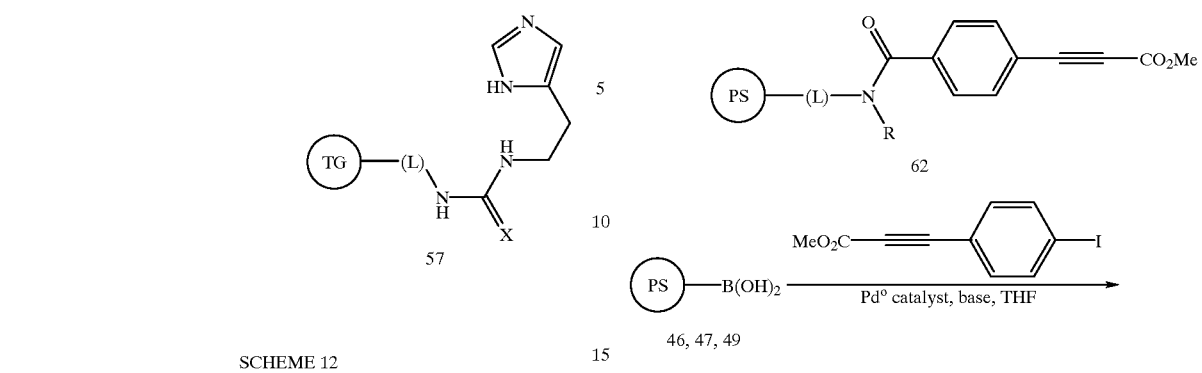
SCHEME 12
Preparations of Polymer-Supported Quenching Dienophiles and Dipolarophiles
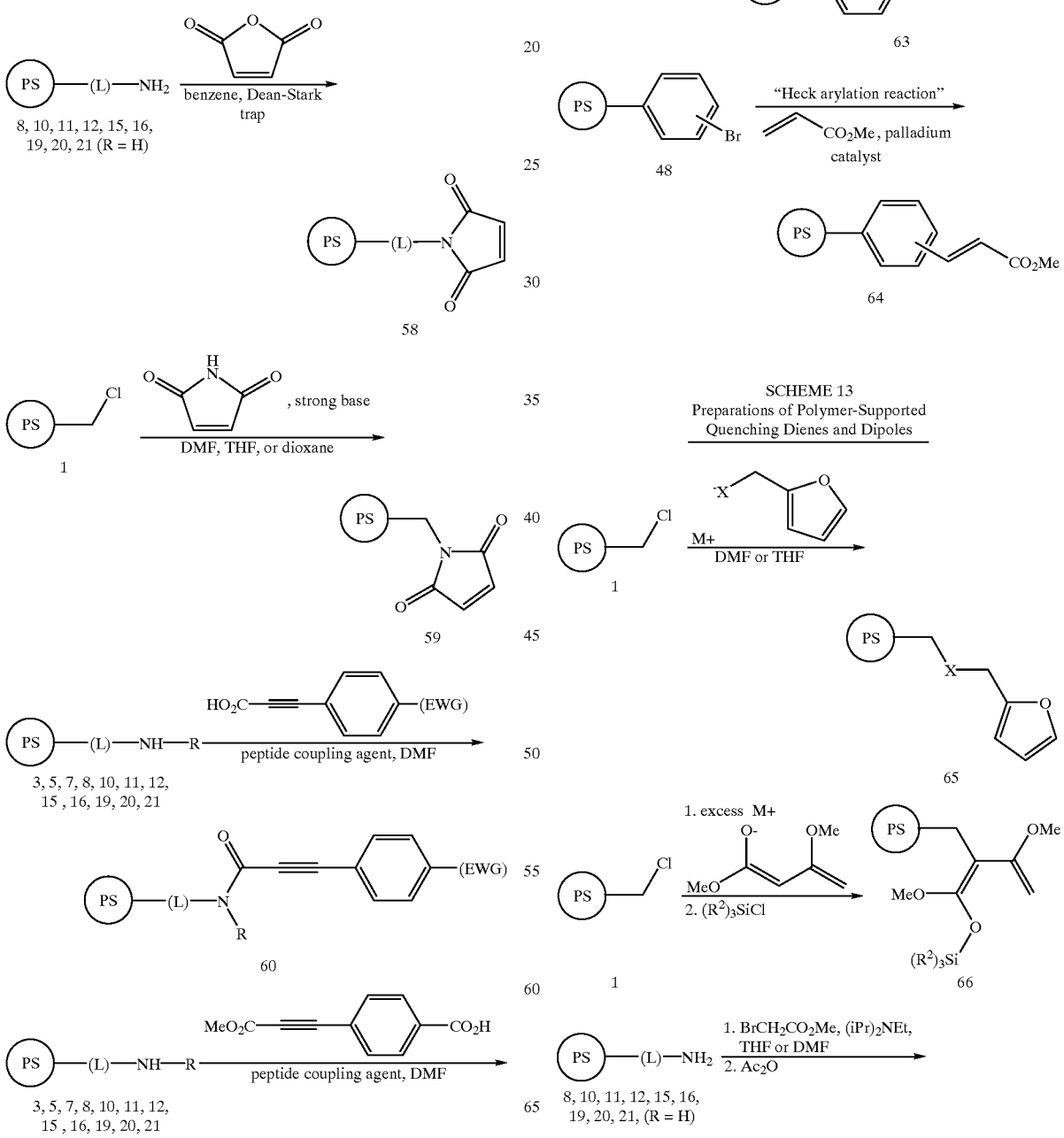

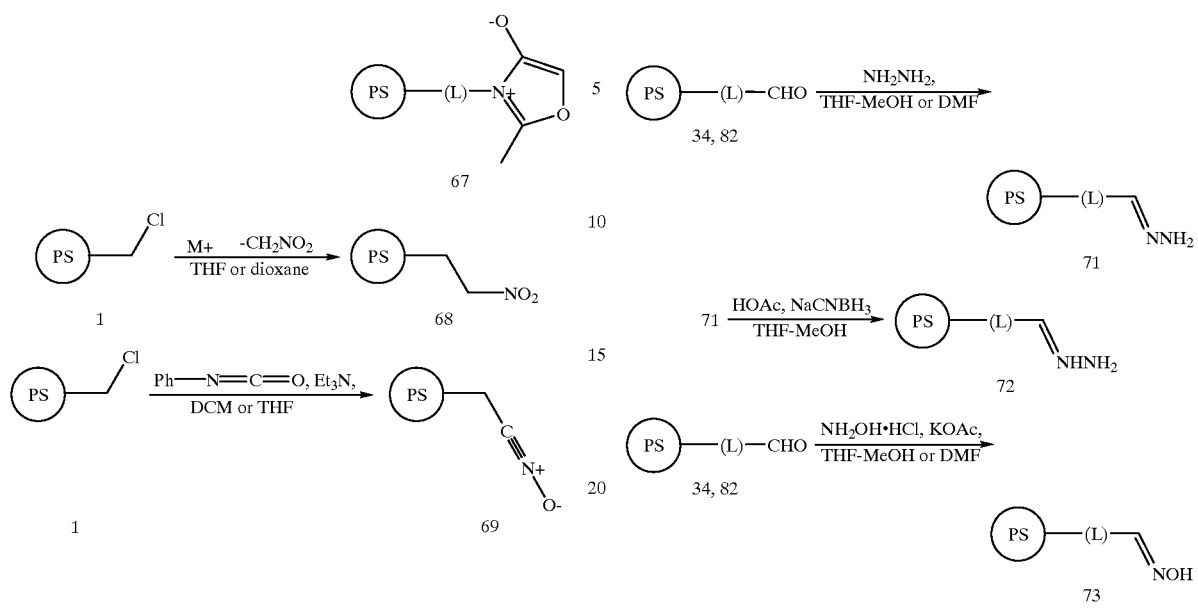
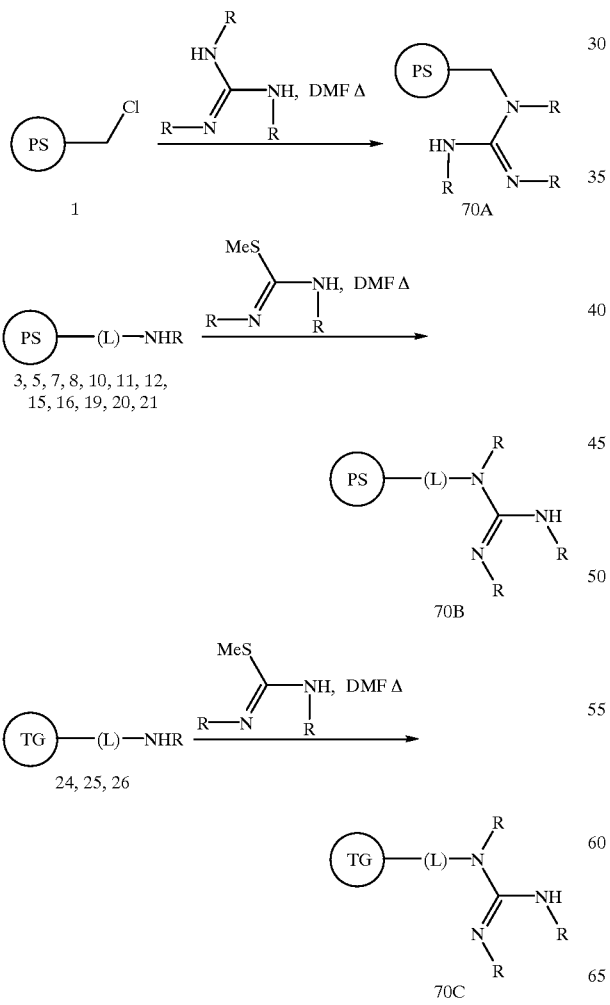

-continued
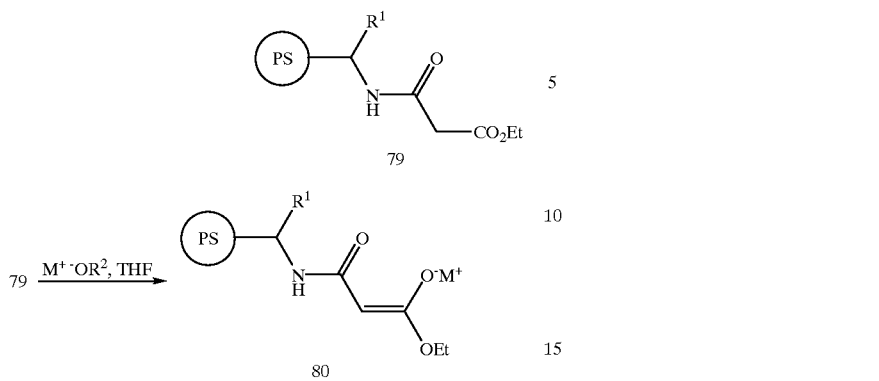
SCHEME 16
Preparations of Polymer-Supported
Quenching Alcohols, Iodides, and Sulfonates
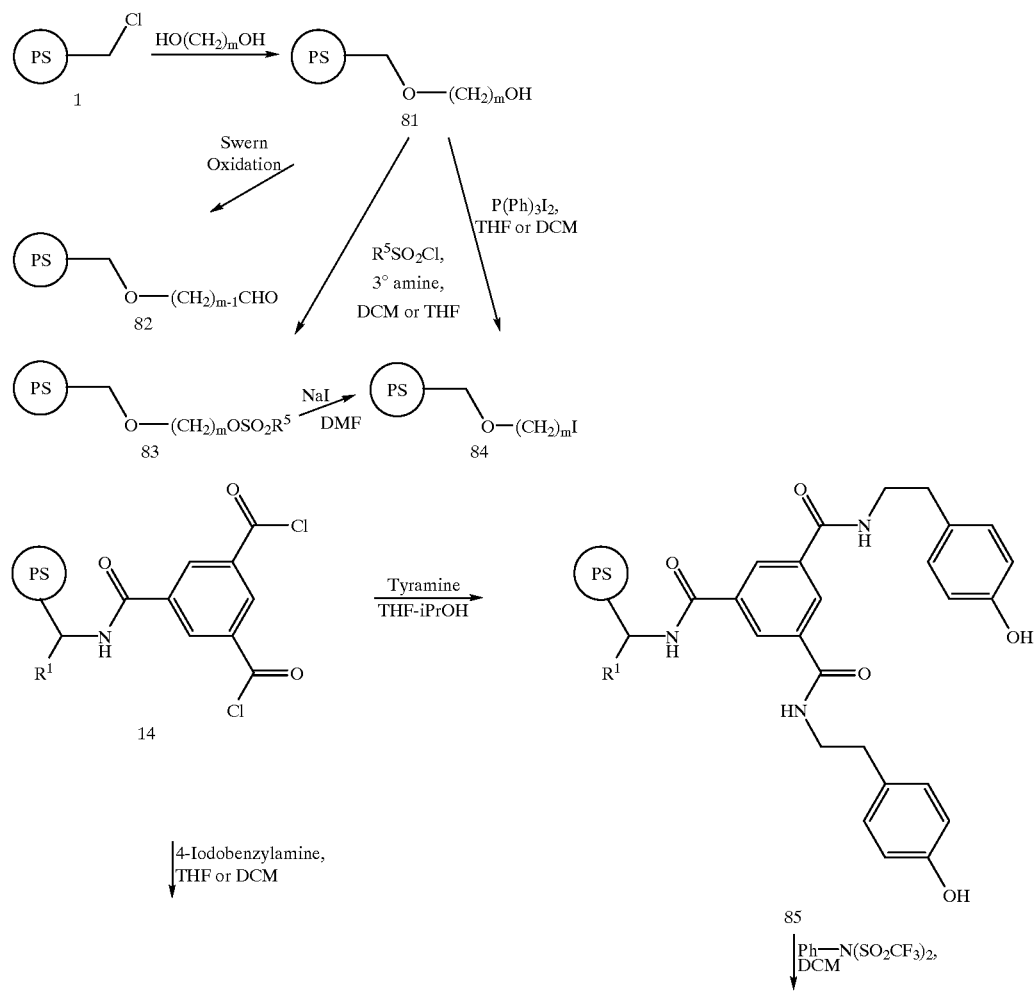

-continued
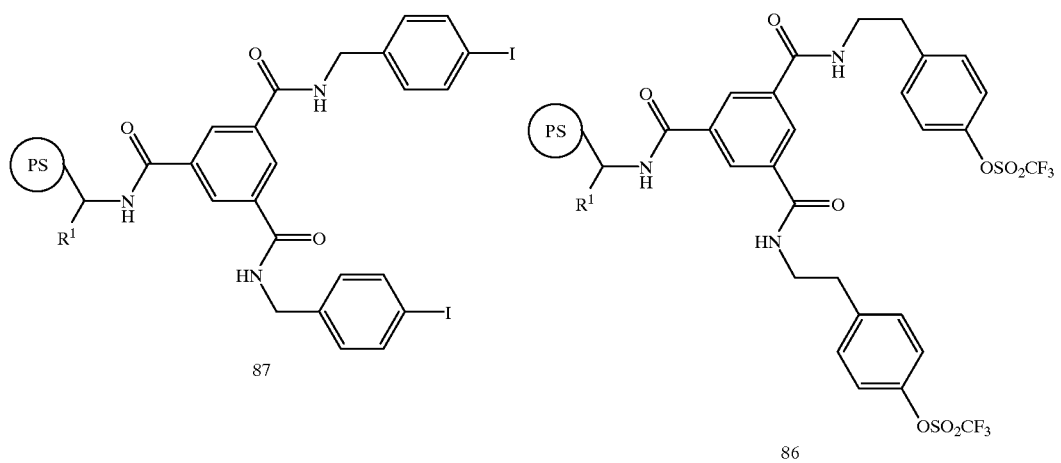
87
86
SCHEME 17
Preparations of Polymer-Supported
Quenching Cyclic Imides and Cyclic Anhydrides
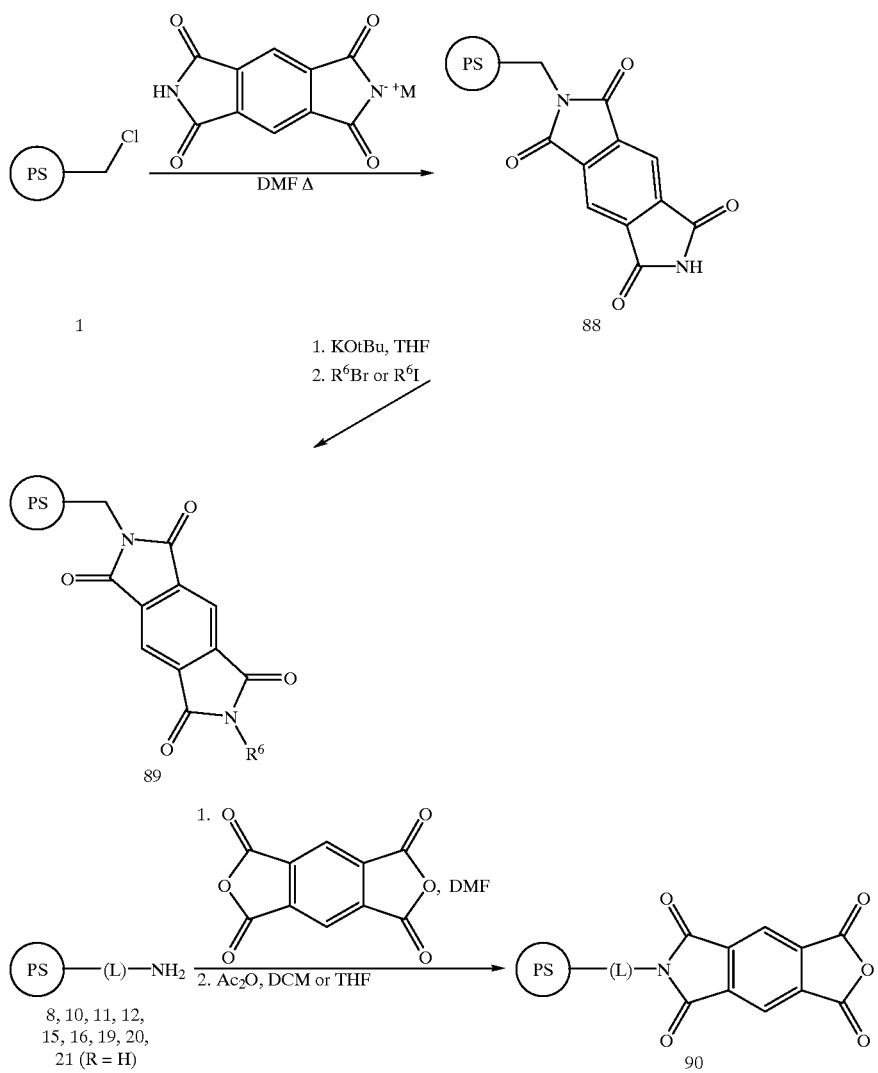

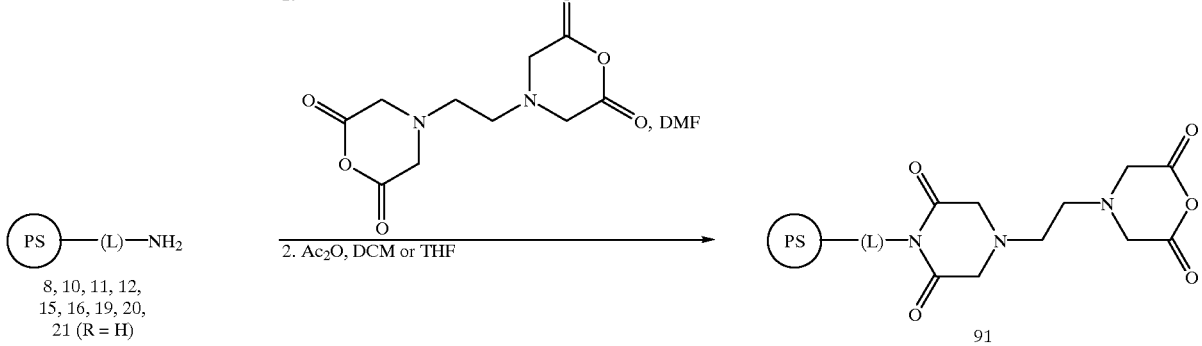

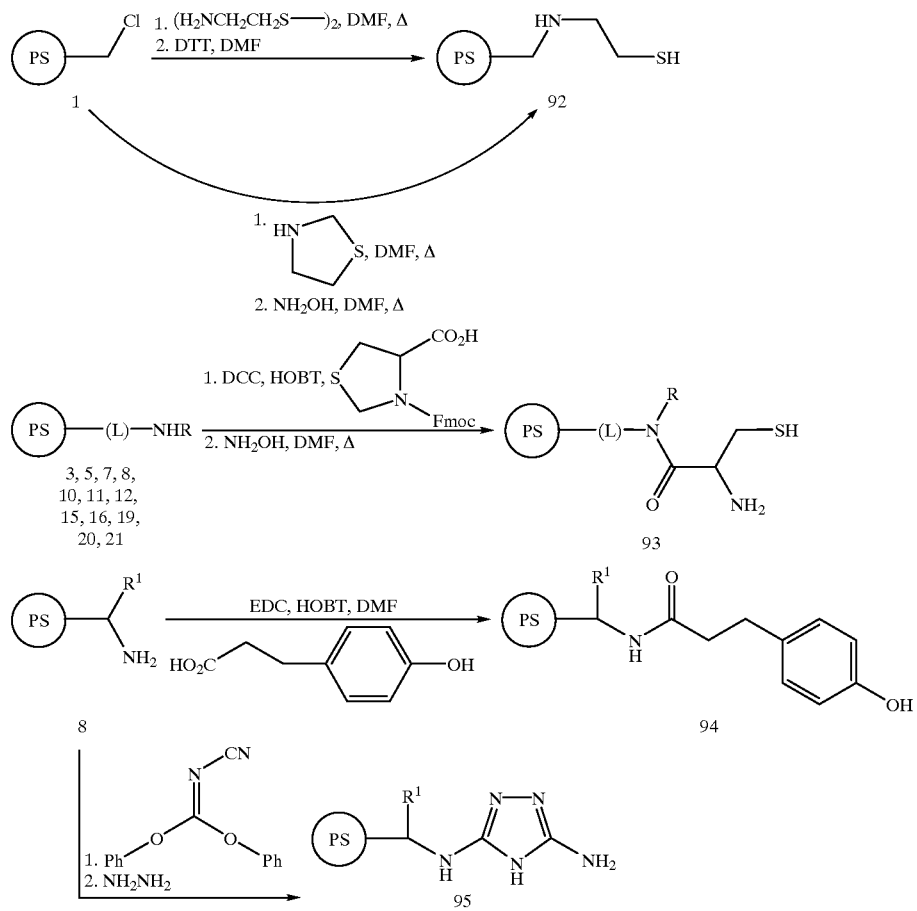

The third aspect of the present invention is the use of polymer-supported quenching reagents, including novel polymer-supported quenching reagents of the present invention and known solid-phase synthesis polymers, for the rapid purification of crude product mixtures of organic reactions. Of particular importance is the use of polymer-supported quench purification as an enabling technology for the preparation of libraries of organic molecules with potential biological activity. Polymer-supported quench has utility in reducing purification time associated with automated parallel organic synthesis, manual combinatorial synthesis and automated combinatorial synthesis. Specific types of chemical transformations that benefit from a polymer-supported quench purification procedure include, but are not limited to, O- and N-acylation, O- and N-sulfonylation, O- and N-phosponylation, O- and N-phoshorylation, C-,O-, N- and S-alkylation, condensation reactions, coupling reactions, cyclization reactions involving two or more components, and the like. The scope of applications of polymer-supported quench is exemplified in Items I–IX below. Representative illustrations of specific cases wherein rapid purification of crude reaction mixtures is achieved with most preferred polymer-supported quenching reagents are described in Examples 19–29. Utility of the polymer-supported quenching reagents and methods described herein is not limited to the reactions described in these examples. On the contrary, the polymer-supported quenching reagents and methods described herein are broadly useful in these and many other organic reactions.

I. Direct Quench (Equations 1.0, 1.1, and 1.2)

Reactant A combines with reactant B to form AB. In order to drive the reaction to completion, B is used in excess (Equation 1.0). The excess reactant is quenched by adding a polymer-supported quenching reagent with A-like properties. Once the excess B is attached to the polymer, it is easily and quickly removed by a simple filtration in those cases where an insoluble polymer is used. In those cases where a soluble polymer is employed, the reaction mixture is first diluted with a solvent that precipitates the polymeric reagent, but not the desired product, and then the precipitated polymer is removed by filtration. The solution fraction contains AB which is enhanced in purity relative to the crude product.

Using this method, the chemist has a choice of whether to use A or B in excess and subsequently to quench with a polymer-supported quenching reagent with B-like or A-like properties, respectively. Additionally, the chemist may choose to add both A-like and B-like polymer-supported quenching reagents to ensure that all starting materials have been removed from the desired product in the event that the reaction did not go to completion, despite using an excess of one starting material.

Alternatively, a reaction between equimolar quantities of A and B may yield a major desired product, AB, and a minor undesired product, AB, (Equation 1.1). AB' may be removed with a polymer-supported quenching reagent that selectively reacts with this undesired product.

One may run analogous combinatorial reactions wherein a diversity of reactants $A^{1-X}$ are reacted with excess of a diversity of reactants $B^{1-Y}$ to form all of the possible AB combinations (Equation 1.2). The combinatorial product mixture is separated from the remaining $B^{1-Y}$ using a single polymer-supported quenching reagent with A-like properties as in the one product case above.

Equation 1.0

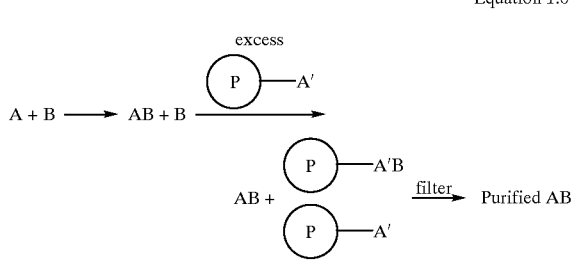

Equation 1.1

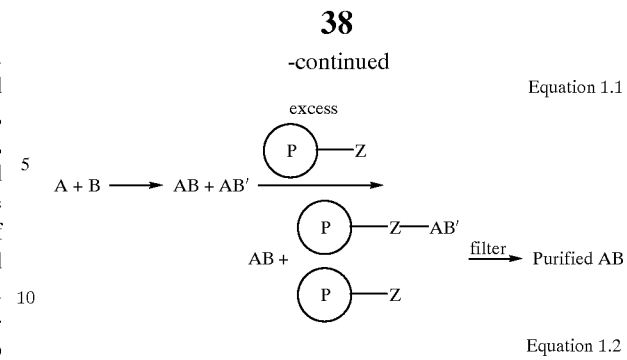

Equation 1.2

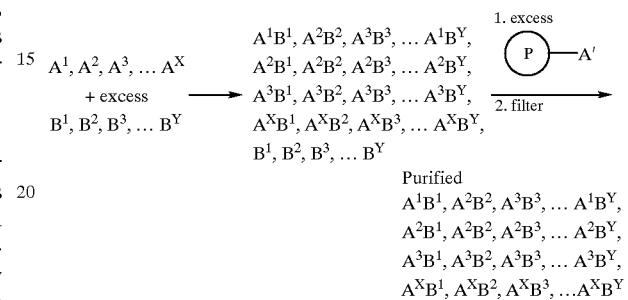

II. Derivative Quench (Equations 2.0 and 2.1)

C reacts with D to form CD (Equation 2.0). In order to drive the reaction to completion, D is used in excess. The excess reagent is derivatized by adding an excess of a third reactant, E. DE and excess E, are quenched by adding a larger excess of a polymer-supported quenching reagent which reacts with both DE and E. The polymeric fraction is then removed by filtration. The solution fraction contains CD which is enhanced in purity relative to the crude product.

This process may be likewise applied in cases where one of the reactants decomposes in a competing side reaction to give a byproduct (Equation 2.1). Thus when C reacts with excess D to form CD and the byproduct $X_D$, the desired product is purified by adding a polymer-supported quenching reagent that selectively derivatives $X_D$ and removing the polymeric fraction by filtration.

Derivative quench by a polymer-supported quenching reagent may be similarly applied in a combinatorial synthesis mode.

Equation 2.0

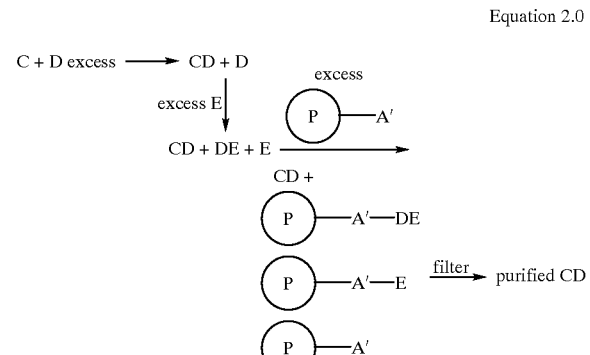

Equation 2.1

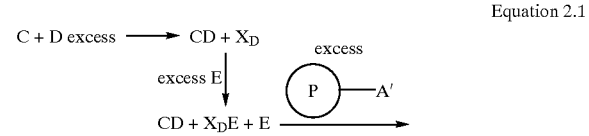

-continued

CD +

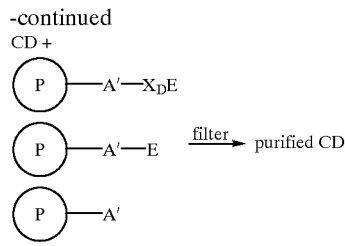 filter→ purified CD

III. Use of Polymer-Supported Quenching Reagents in Conjunction with Polymer-Supported Reactants (Equation 3.0)

A reaction which employs two soluble reactants F and G and one polymer-supported reactant, J, is run in such a fashion that G and polymer-supported-J are used in excess. The desired product, FG, is rapidly purified by adding a larger excess of a polymer-supported quenching reagent with F-like properties which consumes the remaining G. Filtration to remove the polymer-supported reactant before adding the polymer-supported quenching reagent is not necessary when insoluble polymers are used but may be required when soluble polymers are employed if a chemical incompatibility exists between the reactant and quench reagent. Filtration of the polymeric fraction gives a solution of FG which is enhanced in purity relative to the crude product.

The use of polymer-supported quenching reagents in conjunction with polymer-supported reactants may be similarly applied in a combinatorial synthesis mode.

Equation 3.0

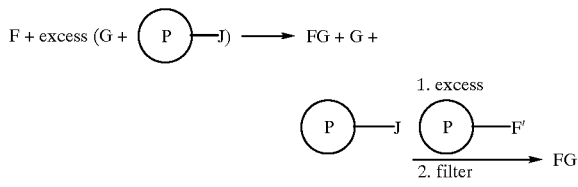

IV. Mixed Polymer-Supported Quench (Equation 4.0)

A reaction which employs multiple reactants (K, L, M, etc.) is run in such a fashion that one of the reactants is limiting. The desired product is rapidly purified from unconsumed reagents by adding polymer-supported quenching reagents; one for each excess reactant. Insoluble polymer-supported quenching reagents may be added sequentially or concurrently. Soluble polymer-supported quenching reagents must be added and removed sequentially unless they are chemically compatible. For this reason, insoluble polymer-supported quenching reagents are preferred for combined use.

Insoluble polymer-supported quenching reagents may also be combined with insoluble ion-exchange resins, chelating resins, silica gel, reversed-phase adsorbents, alumina, activated charcoal, and the like which make non-covalent interactions with impurities as desired in order to increase the efficiency of the purification step. Upon filtration, a purified solution of N is isolated.

Such use of a mixture of solid quenching reagents is equally effective in a combinatorial synthesis mode.

Equation 4.0

K + excess (L + M + etc) 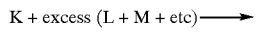

-continued

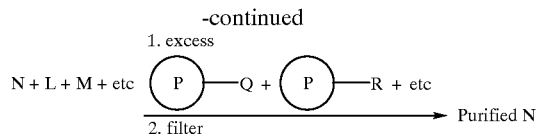

V. Combined Polymer-Supported Reactant and Quench Reagent (Equation 5.0)

A polymer-supported quenching reagent may perform a dual role in purifying the product of one reaction and causing a subsequent synthetic transformation as a polymer-supported reagent. Thus A reacts with excess B to form C. Polymer-supported-D quenches the excess B and also converts product C to product E. This dual role is equally applicable in a combinatorial synthesis mode.

Equation 5.0

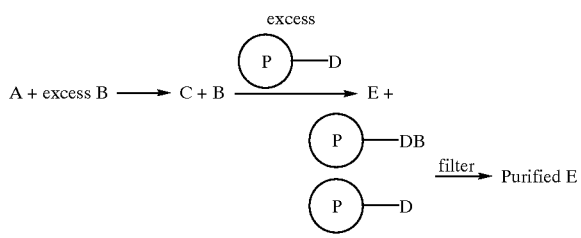

VI. Multistep Syntheses With Polymer-Supported Quench Purifications

Using methodologies described in Equations 1–5 above and variations thereof, individual synthetic transformations may be sequentially combined to give linear or convergent, multistep syntheses. Similar reactions may be run individually in parallel arrays, manually or with the aid of a liquid handling robot, to give single products or alternatively, they may be run in a combinatorial mode to give product mixtures. Polymer-supported quench purification may be applied at each intermediate step or at the conclusion of two or more synthetic steps as is appropriate. An individual who is skilled in the art of organic synthesis will be able to determine whether it is most expedient to purify at each step or to combine polymer-supported quench reagents for the removal of accumulated byproducts and excess reagents from two or more steps in one purification step.

VII. Polymer-Supported Quench Via Columns

As an alternative to adding the polymer-supported quenching reagent(s) to the reaction mixture, insoluble quenching reagent(s) may be packed into solid-phase extraction columns such as, for example, glass or inert plastic chromatography columns, and the like known to those skilled in the art or attached to the interior surface of a capillary column. The crude reaction mixture is eluted through the column. The column volume, the elution rate, and the number of passes through the column are optimized so that a solution of purified product(s) elutes from the column.

VIII. Polymer-Supported Quenching Filters

As an alternative to adding the polymer-supported quenching reagent(s) to the reaction mixture, insoluble quenching reagent(s) may be prepared in the form of porous filter discs or porous membranes. The reaction mixture is allowed to pass through the polymer-supported quenching filter at a rate that results in complete removal of impurities. A single filter may be used or several filters may be combined in series. The crude reaction mixture may be recycled through the filter as necessary to complete the removal of impurities.

IX. Polymer-Supported Quench in a Diversomer® Apparatus

Rapid purification by polymer-supported quench may be carried out using a Diversomer® apparatus as described in U.S. Pat. No. 5,324,483 (which is hereby incorporated by reference) provided that insoluble polymers are employed. The polymer-supported quench reagent is loaded into the pins which are assembled into the pin holder. Reactions are run in individual vials. When the reactions are complete as judged by GC, TLC or HPLC the pins are lowered into the reaction solution and clamped into place. Shaking or other agitation is applied until all excess reagents are consumed. The pins are raised slightly, rinsed into their respective vials and removed. The vials then contain purified product solutions which can be concentrated and/or divided for subsequent transformations.

The polymer-supported quench reagents and rapid purification methods of the instant invention have, for example, the following advantages over existing methods for automated organic synthesis and combinatorial chemistry:

1. A single polymer-supported quench reagent can remove many different types of reactants and byproducts hence customized reagent development time is minimized and quench reagents may be produced in bulk at decreased cost.
2. No resin attachment site needed in target molecule.
3. Solution phase synthesis results in minimal synthetic development time since more solution phase reactions are known than solid phase reactions.
4. One can choose the limiting reagent in any particular reaction based on the value of the reagent and/or nature of the reaction.
5. Convergent syntheses are possible.
6. Solutions of synthetic intermediates are easily divided into aliquots for automated parallel and combinatorial syntheses by liquid handling robots.
7. The use of resin swelling solvents is not required.
8. Reaction progress and product may be analyzed by traditional chromatographic and spectrographic methods.
9. Lack of resin cleavage reaction avoids resin-derived impurities in final product.
10. Greater product amounts may be synthesized in a given reactor volume as compared to polymer-supported synthesis.
11. A smaller excess of reagent can be used to drive reactions to completion compared to the excess required by solid-supported synthesis.
12. Reactive, volatile, toxic wastes are neutralized to nonhazardous solids by the resin and thereby waste disposal is facilitated.

TABLE 2

Purification Using Polymer-Supported Quenching Reagents

| Quenching Reagent | Removes |
|---|---|
| 3 (R = H, n = 2) [PS-CH2-NH-CH2CH2-N(CH2CH2NH2)2] | Acid Chlorides, Acid Anhydrides, Activated Esters, Imidazolides, Isocyanates, Isothiocyanates, Sulfonyl Chlorides, Phosphonyl Chlorides, Phosphoryl Chlorides, Alkyl Halides, Alkylsulfonates, Meerwein Reagent, Epoxides, Enones, α,β-Unsaturated Esters, Pseudothioureas, Aldehydes, Ketones, and the like |
| 24 (R = H, n = 2) [TG-O-C(=O)-NH-CH2CH2-N(CH2CH2NH2)2] | Acid Chlorides, Acid Anhydrides, Activated Esters, Imidazolides, Isocyanates, Isothiocyanates, Sulfonyl Chlorides, Phosphonyl Chlorides, Phosphoryl Chlorides, Alkyl Halides, Alkylsulfonates, Meerwein Reagent, Epoxides, Enones, α,β-Unsaturated Esters, Pseudothioureas, Aldehydes, Ketones, and the like |

TABLE 2-continued

Purification Using Polymer-Supported Quenching Reagents

| Quenching Reagent | Removes |
|---|---|
| 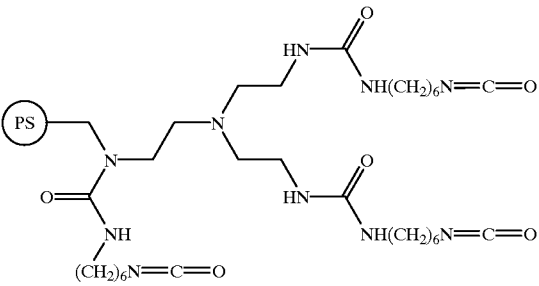 27 (X = O, n = 6, (L) is derived from 3 wherein n = 2 and $R^1$ = H) | 1° and 2° Amines, Alcohols, Carboxylic Acids, Guanidines, Amidines, Hydrazines, Acid Hydrazides, Hydroxylamines, Alkoxyamines, Thiols, and the like |
| 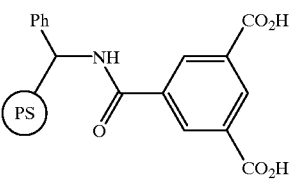 33 ($R^1$ = Ph) | Alkyl Halides, Alkylsulfonates, Diazoalkanes, α-Haloketones, Silyl Chlorides, Silyl Triflates, and the like |
| 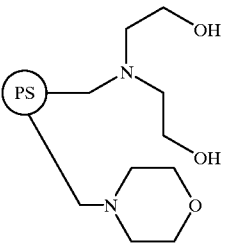 36A ($R^3$ = morpholine, p = 3) | Boronic Acids, Alkyl Halides, Alkylsulfonates, Diazoalkanes, α-Haloketones, Meerwein Reagent, Silyl Chlorides, Silyl Triflates, Acid Chlorides, Acid Anhydrides, Activated Esters, Imidazolides, Isocyanates, Isothiocyanates, Sulfonyl Chlorides, Phosphonyl Chlorides, Phosphoryl Chlorides, and the like |
| 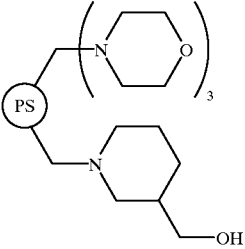 36F ($R^3$ = morpholine, p = 3) | Alkyl Halides, Alkylsulfonates, Meerwein Reagent, α-Haloketones, Silyl Chlorides, Silyl Triflates, Acid Chlorides, Acid Anhydrides, Activated Esters, Imidazolides, Isocyanates, Isothiocyanates, Sulfonyl Chlorides, Phosphonyl Chlorides, Phosphoryl Chlorides1 and the like |

TABLE 2-continued

Purification Using Polymer-Supported Quenching Reagents

| Quenching Reagent | Removes |
|---|---|
| 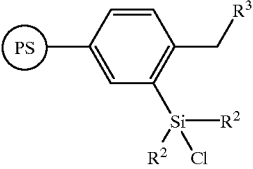<br>38 ($R^3$ = morpholine, $R^2$ = iPr) | Alcohols, Carboxylic Acids, Thiols, Silanols, Phenols, Carbanions, 1° and 2° Amines, and the like |
| 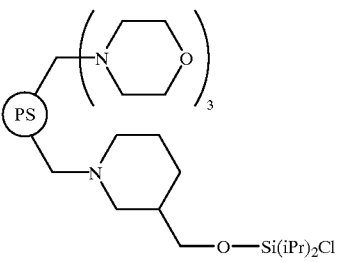<br>40 ($R^3$ = morpholine, p = 3, $R^2$ = iPr) | Alcohols, Carboxylic Acids, Thiols, Silanols, Phenols, Carbanions, 1° and 2° Amines, and the like |
| 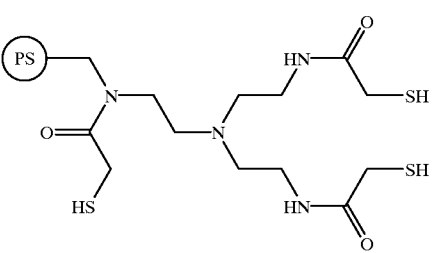<br>45 ((L) is derived from 3 wherein n = 2 and $R^1$ = H) | Alkyl Halides, Alkylsulfonates, α-Haloketones, Meerwein Reagent, Silyl Chlorides, Silyl Triflates, Epoxides, Oxidants, Thiols, Disulfides, and the like |
| 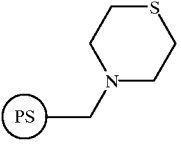<br>44 | Oxidants and the like |
| 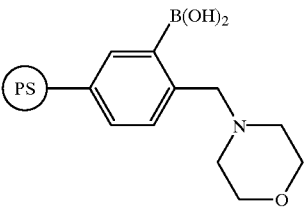<br>46 ($R^3$ = morpholine) | Aryl Iodides, Aryl Bromides, Aryl Triflates, Vinyl Iodides, Vinyl Bromides, Vinyl Triflates, and the like |

TABLE 2-continued

Purification Using Polymer-Supported Quenching Reagents

| Quenching Reagent | Removes |
|---|---|
| 53 ($R^4 = NH_2$, (L) is $CH_2$) [PS-CH$_2$-NH-C(=S)-NH$_2$] | Alkyl Halides, Alkylsulfonates, α-Haloketones, Meerwein Reagent, and the like |
| 54 ((L) is derived from 3 wherein n = 2) [PS-CH$_2$-N(C(=O)CH$_2$-imidazole)-CH$_2$CH$_2$-N(CH$_2$CH$_2$NHC(=O)CH$_2$-imidazole)$_2$] | Aldehydes, Ketones, Imines, Alkyl Halides, Alkylsulfonates, Isocyanates, Isothiocyanates, Chloroformates, Phosgene, Thiophosgene, and the like |
| 59 [PS-CH$_2$-maleimide] | Dienes, Dipoles, Sulfides, 1° and 2° Amines, and the like |
| 65 (X = S) [PS-CH$_2$-S-CH$_2$-furan] | Dienophiles, Dipolarophiles, $Cl_2$, $Br_2$, $I_2$, Oxidants, and the like |
| 70A (R = H) [PS-CH$_2$-NH-C(=NH)-NH$_2$] | Acid Chlorides, Acid Anhydrides, Activated Esters, Imidazolides, Isocyanates, Isothiocyanates, Sulfonyl Chlorides, Phosphonyl Chlorides, Phosphoryl Chlorides, Alkyl Halides, Alkylsulfonates, Meerwein Reagent, Epoxides, Enones, α,β-Unsaturated Esters, α-Diketones, β-Diketones, β-Keto Esters, and the like |

TABLE 2-continued

Purification Using Polymer-Supported Quenching Reagents

| Quenching Reagent | Removes |
|---|---|
| 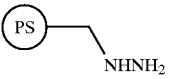<br>72 ((L) = CH$_2$) | Aldehydes, Ketones, Enones, α,β-Unsaturated Esters, α-Diketones, β-Diketones, β-Keto Esters, Acid Chlorides, Acid Anhydrides, Activated Esters, Imidazolides, Isocyanates, Isothiocyanates, Sulfonyl Chlorides, Phosphonyl Chlorides, Phosphoryl Chlorides, Alkyl Halides, Alkylsulfonates, Meerwein Reagent, Epoxides, and the like |
| 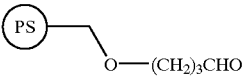<br>82 | Carbanions, primary amines, Hydroxylamine, Alkoxyamines, Hydrazines, Glycols, 1,3-Diols, 1,2-Dithiols, 1,3-Dithiols, 1,2-Aminoalcohols, 1,3-Aminoalcohols, 1,2-Aminothiols, 1,3-Aminothiols, Hydride Reducing Agents, and the like |
| 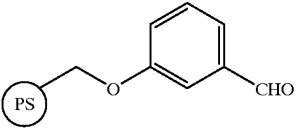<br>34A | Carbanions, primary amines, Hydroxylamine, Alkoxyamines, Hydrazines, Glycols, 1,3-Diols, 1,2-Dithiols, 1,3-Dithiols, 1,2-Aminoalcohols, 1,3-Aminoalcohols, 1,2-Aminothiols, 1,3-Aminothiols, Hydride Reducing Agents, and the like |
| 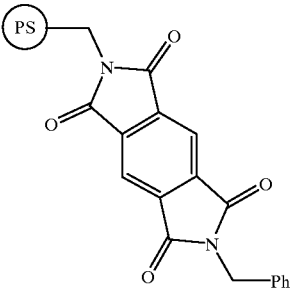 | Carbanions, Hydroxides, Alkoxides, 1° and 2° Amines, Hydride Reducing Agents, and the like |
| 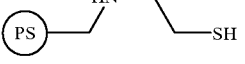<br>92 | Alkyl Halides, Alkylsulfonates, α-Haloketones, Meerwein Reagent, Silyl Chlorides, Silyl Triflates, Epoxides, Oxidants, Thiols, Disulfides, Ketones, Aldehydes, and the like |
| 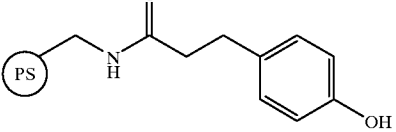<br>94<br>(R$^1$ = H) | Halogens, Carbocations, Electrophilic reagents, and the like |
| 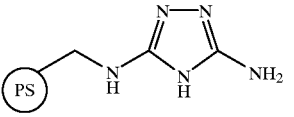<br>95<br>(R$^1$ = H) | β-diketones, β-ketoesters, β-ketoamides, Vinylogous esters, Vinylogous amides, α-ketoesters, α-ketoamides, α-diketones, α-haloketones |

EXAMPLE 1

Preparation of Quenching Amine Resin

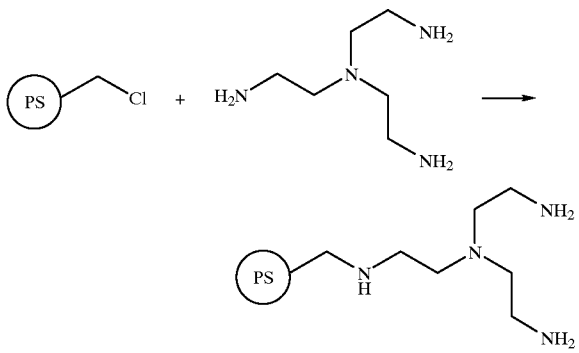

A suspension of Merrifield resin (50 g, 1.7 mmol Cl/g resin, 85 mmol) in DMF (500 mL) was treated with tris(2-aminoethyl)amine (50 mL, 342 mmol). The resulting mixture was shaken at 65° C. for 6 hours under $N_2$ atmosphere. After cooling to room temperature, the resin was filtered and washed successively with MeOH, DMF, $Et_3N$, MeOH, DCM, $Et_3N$, MeOH, DCM, MeOH, DCM, and MeOH. The resulting amine resin was dried at 45° C. to 50° C., 20 mmHg for 24 hours and stored in tightly sealed bottles.

Calc'd: N, 8.02; Cl, 0.00.
Found: N, 5.96; Cl, 0.42 (indicates approx. 25% crosslinking).

A small sample reacted with excess 3,4-dichlorophenyl isocyanate in DCM indicates a quenching capacity of 3.18 mmol/g resin, consistent with ¾ of the N content in the amine resin.

Calc'd: N, 6.51; Cl, 14.15.
Found: N, 6.25; Cl, 13.99.

EXAMPLE 2
Preparation of Quenching Acid Chloride Resin

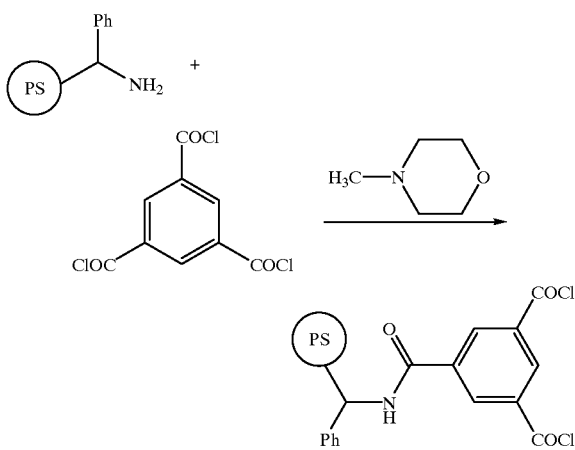

A suspension of Benzhydrylamine.HCl resin (2 g, 0.83 mmol N/g resin, 1.66 mmol) in DCM (20 mL) was treated with N-methylmorpholine (1.2 mL, 10.9 mmol) and mixed briefly before adding a solution of benzene-1,3,5-tricarboxylic acid chloride (Aldrich, 0.93 g, 3.5 mmol). The resulting mixture was stirred at room temperature for 1 hour, diluted with DCM (200 mL), and filtered. The resin was subsequently washed with five cycles of DCM followed by EtOAc and dried at 35° C. to 40° C., 20 mmHg for 24 hours. Proof of product was demonstrated by continuing as in Example 3 below.

EXAMPLE 3

Preparation of Quenching Carboxylic Acid Resin

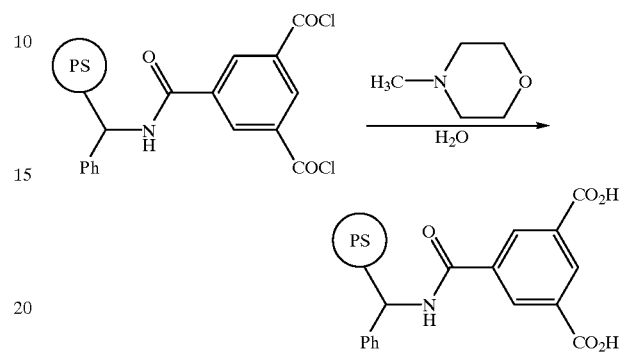

Example 2 was repeated except at the conclusion of the 1 hour reaction period, the resulting mixture was diluted with dioxane (25 mL), water (10 mL), and N-methylmorpholine (2 mL). After stirring 1 hour at room temperature, the resin was collected by filtration and washed with MeOH, water, dioxane, DCM, (4% TFA in DCM)×4, DCM, MeOH, DCM, MeOH, DCM, MeOH, MeOH. The resulting resin was dried at 45° C., 25 mmHg for 60 hours. A ninhydrin test of the resin is negative for free amine.

Calc'd: N, 0.94; Cl, 0.00.
Found: N, 1.57; Cl, 0.05.
IR 1732 (COOH).

EXAMPLE 4

Preparations of Quenching Isocyanate Resin

A. Low Loading Isocyanate Resin

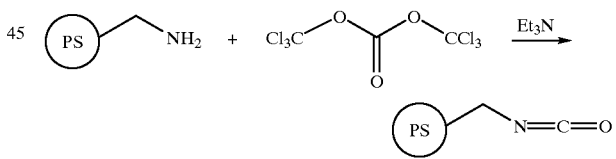

A suspension of benzylamine resin (0.56 mmol N/g resin, 7.5 g, 4.2 mmol) in DCM (80 mL) was treated with $Et_3N$ (6 mL, 43 mmol) and triphosgene (1.3 g, 13 mmol equivalents of phosgene) and shaken 6 hours at room temperature. The resulting isocyanate resin was filtered and washed with (DCM, EtOAc)×4, $Et_2O$. The resin was then dried at 35° C. to 40° C., 25 mmHg for 24 hours.

IR (KBr) 2257 (N=C=O).

B. High Loading Isocyanate Resin

The procedure for the low loading isocyanate resin was repeated with benylamine resin (2.0 mmol N/g resin) prepared by the method of Zikos C. C. and Frederigos N. G., (*Tetr. Lett.*, 1995;36:3741–44).

IR (KBr) 2257 (N=C=O).

EXAMPLE 5
Preparation of Amine/Aminoalcohol Resin

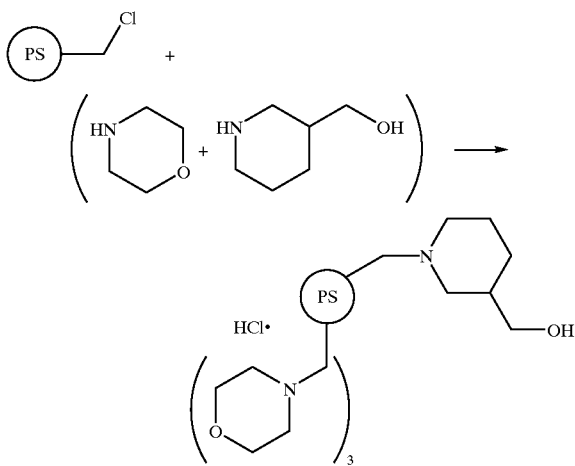

A solution of morpholine (5.2 mL, 60 mmol), 3-hydroxymethylpiperidine (2.3 g, 20 mmol) and DMF (35 mL) was added to Merrifield resin (5 g, 4.3 mmol Cl/g resin, 21.5 mmol). The resulting mixture is shaken at 65° C. for 6 hours under $N_2$ atmosphere. After cooling to room temperature, the resin was filtered and washed successively with DMF, MeOH, $Et_3N$, DMF, MeOH, $Et_3N$, MeOH, DCM, MeOH, DCM, EtOAc, EtOAc. The resulting amine/aminoalcohol resin is dried at 45° C. to 50° C., 20 mmHg for 24 hours and stored in tightly sealed bottles.
Calc'd: N. 4.83; Cl, 0.00.
Found: N, 4.83; Cl, 0.18.

A small portion was treated with excess 2-bromobenzoyl chloride in DCM and worked up as above. Bromine analysis is consistent with a 3:1 ratio of morpholine to 3-hydroxymethylpiperidine attached to the resin.
Calc'd: Br, 5.59.
Found: Br, 5.54.

EXAMPLE 6
Preparation of Quenching Chlorosilane Resin

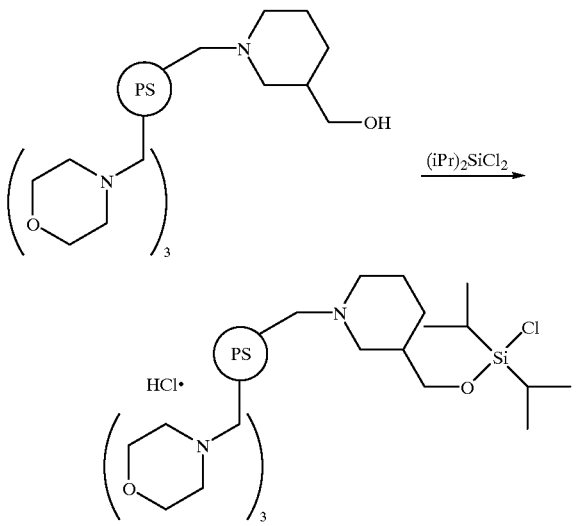

The amine/aminoalcohol resin prepared in Example 5 is suspended in DCM and treated with 3 equivalents of diisopropyl-dichlorosilane. After stirring for 1 hour at room temperature, the solvent is removed by filtration, and the resin is rinsed five times with DCM, dried in vacuo, and stored in tightly sealed bottles prior to use.

EXAMPLE 7
Preparations of Quenching Thiol Resin

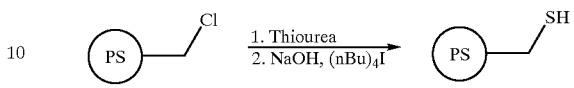

Prepared as described by Frechet J. M., et al., Polymer, 1979;20:675–80.

EXAMPLE 8
Preparation of Quenching Aminothiol Resin

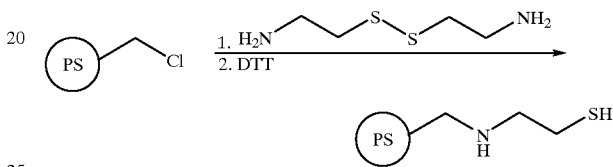

Cystamine dihydrochloride (3.8 g, 16.9 mmol) was dissolved in 1N NaOH (34 mL). The solution was extracted repeatedly with dichloromethane (10×25 mL). Combined organic extracts were dried over $MgSO_4$ and evaporated to an oil (2.3 g). The oil was dissolved in DMF (30 mL) and added to Merrifield resin (1.7 mmol Cl/g resin, 3 g). The resulting slurry was warmed to 65° C. under $N_2$ in a rotated flask for 4 hours. The resin was collected by filtration and washed successively with DCM, MeOH, $Et_3N$, DCM, $Et_3N$, MeOH, DCM, MeOH, DCM, MeOH. The resin was dried overnight at 40° C. to 45° C., 20 mm Hg and a portion (2 g) was subsequently suspended in DMF (20 mL). The suspension was treated with dithiothreitol (3.6 g) and deoxygenated by evacuating the flask and repressurizing with $N_2$ gas several times. The mixture was warmed to 65° C. for 2 hours then allowed to stand at room temperature under $N_2$ overnight. The resin was collected by filtration and washed with MeOH, DCM, MeOH, DCM, MeOH, DCM, DCM, hexanes, hexanes then dried at 40° C. to 45° C., 20 mm Hg for 24 hours.
Calc'd: N, 2.22; S, 5.08.
Found: N, 2.01; S, 4.44.

EXAMPLE 9
Preparation of Quenching Thioether Resin

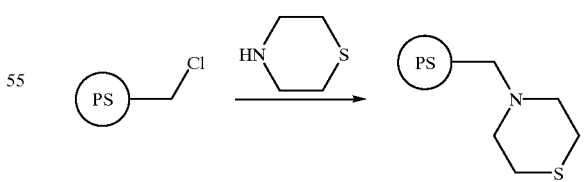

A suspension of Merrifield resin (5 g, 4.3 mmol Cl/g resin, 21.5 mmol) in DMF (40 mL) was treated with thiomorpholine (6 mL, 59.7 mmol). The resulting mixture was shaken at 65° C. for 4 hours under $N_2$ atmosphere, then allowed to stand at room temperature overnight. $Et_3N$ (2 mL) was added, and the slurry was shaken at 65° C. for 2 hours. After cooling to room temperature, the resin was filtered and washed successively with MeOH, DMF, Et₃N, DCM, MeOH, Et₃N, DCM, MeOH, DCM, MeOH, DCM, and MeOH. The resulting thiomorpholine resin was dried at 45° C. to 50° C., 20 mmHg for 48 hours and stored in tightly sealed bottles.

Calc'd: N, 4.70; S, 10.74; Cl, 0.00.
Found: N, 4.59; S, 10.77; Cl, 0.17.

EXAMPLE 10
Preparations of Quenching Guanidine Resin
A. Low Loading Guanidine Resin

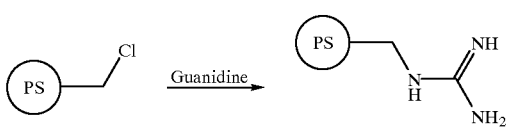

To a suspension of Merrifield resin (5 g, 1.7 mmol Cl/g resin) in DMF (100 mL) is added guanidine hydrochloride (5 g) and a 1 M solution of KOtBu in THF (50 mL). The reaction mixture is heated at 90° C. to 100° C. for 24 hours. Once cooled, the resin is filtered and washed with DMF/DBU (70/30), DMF, dioxane, water, THF, and Et₂O. The resin is dried under vacuum. This procedure is then repeated to give the desired product:

B. High Loading Guanidine Resin

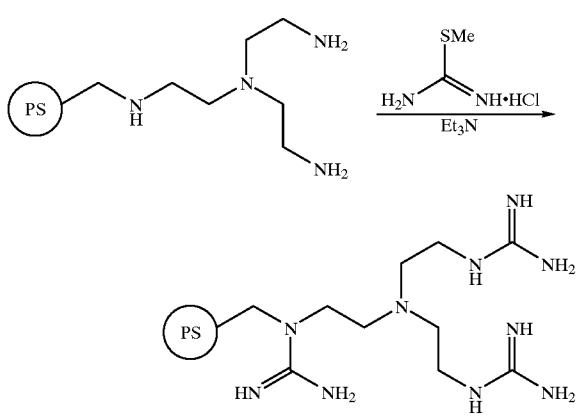

A solution of thiourea (90 mmol) in DMF (100 mL) is treated with MeI (85 mmol) and stirred 2 hours at room temperature. The resulting solution is treated with the amine resin from Example 1 (10 g, 31.8 mmol) and Et₃N (90 mmol). The reaction mixture is warmed to 80° C. for 4 hours then cooled to room temperature before filtering and washing with MeOH, DMF, Et₃N, MeOH, DCM, Et₃N, MeOH, DCM, MeOH, DCM, MeOH, MeOH. The resulting guanidine resin is dried at 45° C., 25 mmHg, for 24 hours and stored in tightly sealed bottles.

EXAMPLE 11
Preparation of Quenching Aminodiol Resin

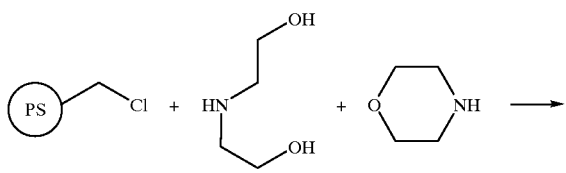

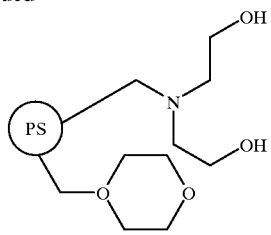

A suspension of Merrifield resin (2 g, 4.3 mmol Cl/g resin, 8.6 mmol) in DMF (20 mL) is treated with diethanolamine (1.5 g, 14.3 mmol) and morpholine (1.2 g, 14.3 mmol). The resulting mixture is shaken at 65° C. for 6 hours under N₂ atmosphere. After cooling to room temperature, the resin was filtered and washed successively with MeOH, DMF, Et₃N, MeOH, DCM, Et₃N, MeOH, DCM, MeOH, DCM, and MeOH. The resulting aminodiol resin is dried at 45° C. to 50° C., 20 mmHg for 24 hours and stored in tightly sealed bottles.

EXAMPLE 12
Preparation of a Quenching Diazomethane Resin

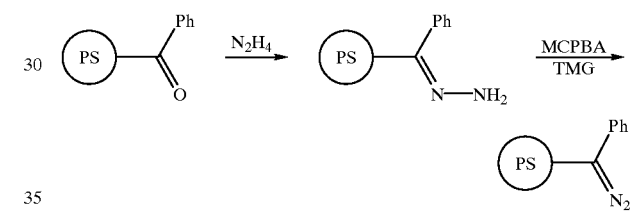

"Polymer diazomethylene" is prepared according to the method of Chapman P. H. and Walker D., *J. Chem. Soc., Chem. Commun.*, 1975:690–1.

EXAMPLE 13
Polymer-Supported N-Methylmorpholine

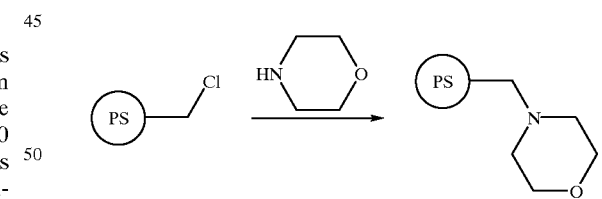

A suspension of Merrifield resin (20 g, 4.3 mmol Cl/g resin, 86 mmol) in DMF (100 mL) was treated with morpholine (20 mL, 229 mmol). The resulting mixture was shaken at 65° C. for 6 hours under N₂ atmosphere, then allowed to stand at room temperature 24 hours. After cooling to room temperature, the resin was filtered and washed successively with MeOH, DMF, MeOH, Et₃N, DCM, MeOH, Et₃N, DCM, MeOH, EtOAc, and Hexanes. The resulting N-methylmorpholine resin was dried at 45° C. to 50° C., 20 mmHg for 48 hours and stored in tightly sealed bottles.

Calc'd.: N, 4.83; Cl, 0.00.
Found: N, 4.98; Cl, 0.21.

EXAMPLE 14
Preparation of Quenching Carboxylic Acid Resin

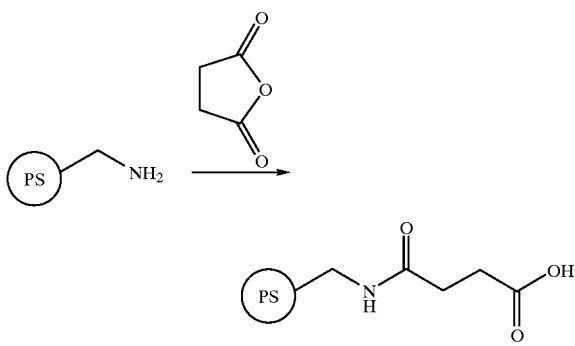

The method of Zikos C. C and Frederigos N. G., (*Tetr. Lett.*, 1995;36:3741–44) was used to prepare aminomethylpolystyrene (3.66 mmol N/g resin). This resin (1.0 g) was treated with a solution composed of succinic anhydride (1.1 g, 11 mmol), DMF (5 mL), and DCM (10 mL). The resulting slurry was mixed at room temperature for 4 hours. The resin was collected by filtration, washed 4 times with alternating portions of if MeOH and DCM, washed with hexanes and dried overnight at 40° C., 20 mm Hg. The resin is gives a negative ninhydrin test.

EXAMPLE 15
Preparation of Quenching Phenol Resin

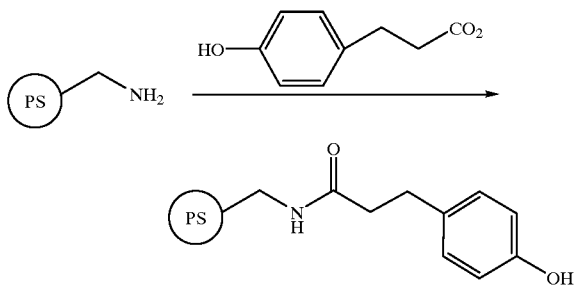

The method of Zikos C. C. and Frederigos N. G., (*Tetr. Lett.*, 1995;36:3741–44) was used to prepare aminomethylpolystyrene (4.5 mmol N/g resin). This resin (1.0 g) was treated with a solution composed of 3-(4-hydroxyphenyl)-propionic acid (2.2 g, 13.3 ,mmol), EDC (2.5 g, 13 mmol), HOBT.H$_2$O (1.8 g) and DMF (20 mL). The resulting slurry was mixed at room temperature for 36 hours. The resin was collected by filtration. It was then successively washed with DCM n) MeOH, MeOH-satNH$_4$OH (1:1), DMF, DCM, MeOH, DCM, hexanes, hexanes. It was dried overnight at 40° C., 20 mm Hg. The resin is gives a negative ninhydrin test.

EXAMPLE 16
Preparation of a Quenching Thiourea Resin

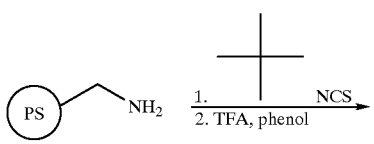

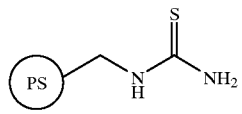

The method of Zikos C. C. and Frederigos N. G., (*Tetr. Lett.*, 1995;36:3741–44) was used to prepare aminomethylpolystyrene (3.66 mmol N/g resin). This resin (2.0 g) was suspended in toluene (20 mL) and treated with t-butylisothiocyanate (2.5 g, 21.7 mmol) and heated at 70° C. overnight. The resin was filtered and rinsed with toluene. It was then resubjected to the same conditions for 2.5 hours further. The resin was collected by filtration and washed 5 times with DCM followed by MeOH. It was dried overnight at 45° C. to 50° C., 20 mm Hg. The resin is gives a negative ninhydrin test. The dried resin was combined with phenol (1 g) and treated with TFA (20 mL), mixing at room temperature for 7.5 hours. The resulting resin was collected by filtration, washed successively with DCM, Et$_3$N, MeOH, DCM, MeOH, DCM, hexanes and dried as before.
Cacl'd: N, 8.43; S, 9.63.
Found: N, 6.22; S, 6.96.

EXAMPLE 17
Preparation of an Aldehyde Quenching Resin

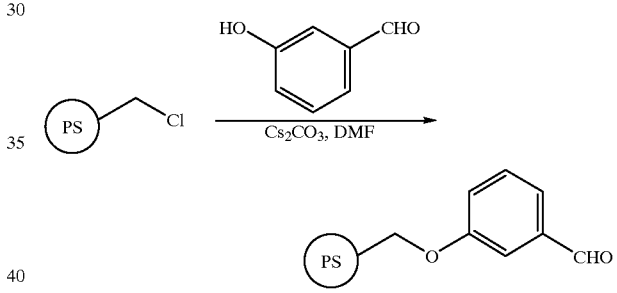

A suspension of Merrifield resin (4.3 mmol Cl/g resin, 5 g) in DMF (100 mL) was treated with 3-hydroxybenzaldehyde (4 g, 32.7 mmol) and Cs$_2$CO$_3$ (10.7 g, 32.7 mmol). This mixture was rotated in a flask at 70° C. to 75° C. under N$_2$ for 24 hours. After cooling, the resin was collected by filtration and washed successively with water (3 times), MeOH, water, dioxane, MeOH, DCM, DCM, hexanes, hexanes and was dried at 55° C., 20 mm Hg overnight to afford 6.88 g of the aldehyde resin.
Calc'd: Cl, 0.00.
Found: Cl, 0.02.

EXAMPLE 18
Preparation of an Aminotriazole Quenching Resin

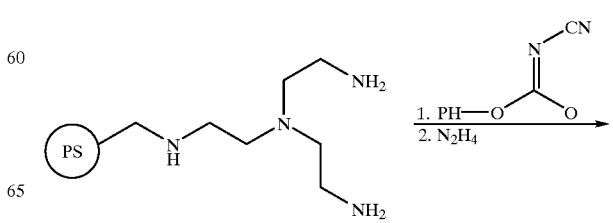

-continued

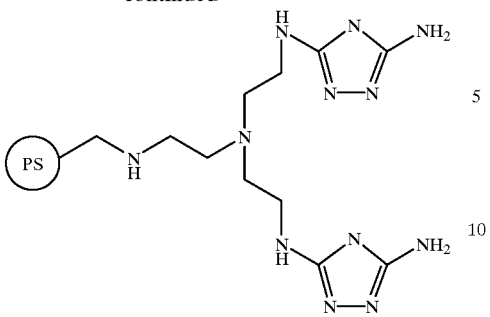

Triethylamine (1 g) and diphenyl cyanocarbon-imidate (2.4 g) were dissolved in dichloromethane (20 mL). Amine resin (from Example 1, 2 g, 1.5 mmol $NH_2$/g resin) was slowly added and the mixture agitated 2 hours at room temperature. The resin was filtered and washed with DCM then MeOH (3 times each), DCM, and hexane. It was then air dried. The resulting resin was then suspended in ethanol (40 mL) and hydrazine monohydrate (1 g) was added. The mixture was refluxed for 30 minutes then filtered hot. The resin was washed with MeOH then DCM (3 times each), then washed with hexane and air dried. Comparison of the N content of the starting resin (5.94% N) with that of the final resin (15.36% N) is consistent with the formation of aminotriazoles at the primary amines of the starting resin.

EXAMPLE 19
Urea Synthesis From Amine and Isocyanate

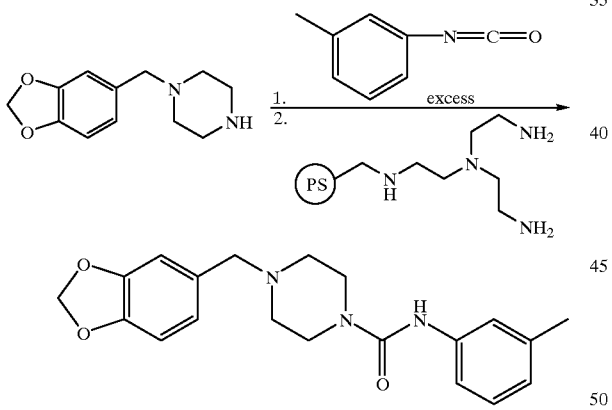

To a solution of 1-piperonylpiperazine (0.36 mmol) in DCM (2 mL) was added m-tolyl isocyanate (0.4 mmol). The reaction mixture was shaken for 2 hours, and then the polymer-supported quenching reagent (100 mg), was added. After shaking for 3 hours, the reaction mixture was left overnight. Filtration and concentration gave the purified product.
MS(CI): 353 (M+).

EXAMPLE 20
Amide Synthesis From Amine and Acid Chloride
A. Excess Acid Chloride Quenched with Polymer-Supported Amine

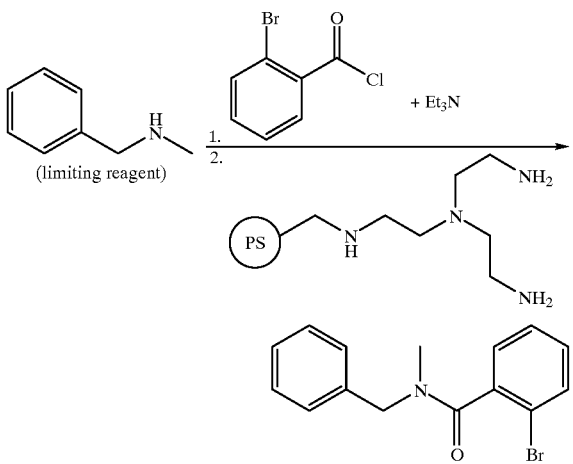

To a solution of N-benzylmethylamine (0.4 mmol) in DCM (1 mL) were added $Et_3N$ (3 mmol) and 2-bromobenzoyl chloride (0.6 mmol). The reaction mixture was shaken for 4 hours, and then the polymer-supported quenching reagent (100 mg) was added. After shaking for 2 hours, the reaction mixture was left overnight. Filtration, concentration, and partition between aqueous NaOH and EtOAc gave the purified product.
MS(CI): 306, 304 (M+1).
B. Excess Amine Quenched With Polymer-Supported Isocyanate

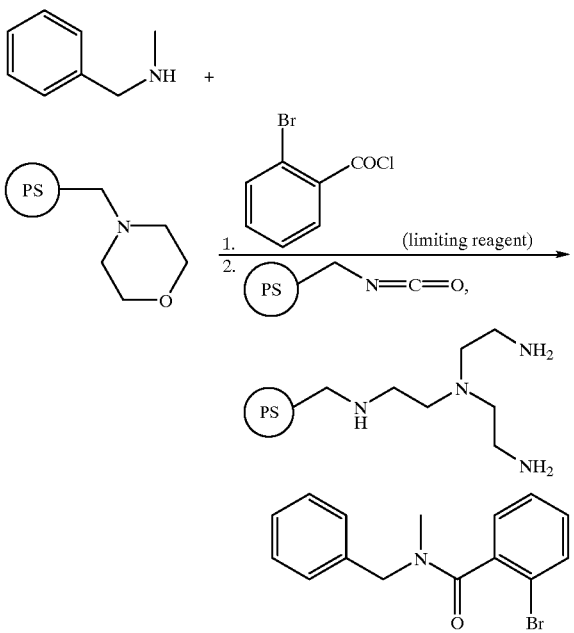

To a suspension of amine resin from Example 1 (0.63 mmol) in DCM (2 mL) were added N-methyl-benzylamine (0.23 mmol) and 2-bromobenzoyl chloride (0.146 mmol). The reaction mixture was shaken for 5 hours. Isocyanate resin from Example 4 (0.2 g) was added followed by DCM (1 mL), and then reaction mixture was shaken for 16 hours. Amine resin from Example 1 (0.08 g) and DCM (1 mL) were added, after 30 minutes filtration and concentration gave the purified product.
MS(CI): 304, 306 (M+1).

EXAMPLE 21

Sulfonamide Synthesis From Amine and Sulfonyl Chloride

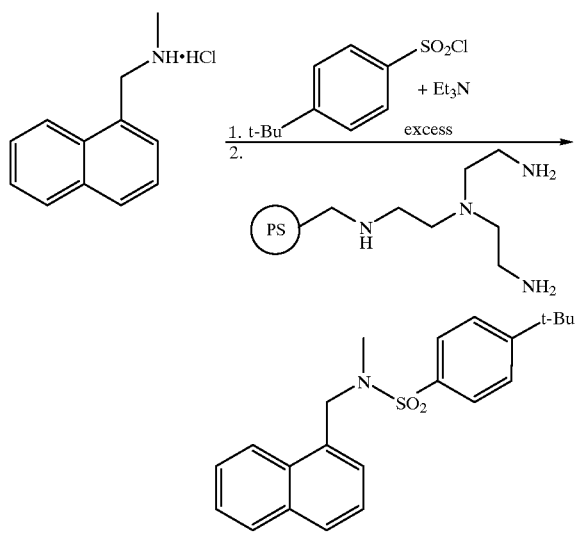

To a solution of N-methyl-1-napthalenemethylamine hydrochloride (0.4 mmol) in DCM (1 mL) were added Et₃N (3 mmol) and a solution of 4-tert-butylbenzenesulfonyl chloride (0.6 mmol) in DCM (I mL). The reaction mixture was shaken for 4 hours, and then the polymer-supported quenching reagent (100 mg) was added. After shaking for 2 hours, the reaction mixture was left overnight. Filtration, concentration, and partition between aqueous sodium hydroxide and DCM gave the purified product.
MS(CI): 368 (M+1).

EXAMPLE 22

Sulfonamide N-Alkylation and Desulfonylation

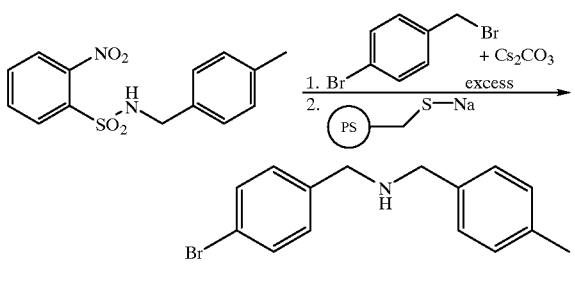

To a solution of the 2-nitrophenylsulfonamide (0.082 mmol) in DMF (0.5 mL) were added cesium carbonate (0.34 mmol) and 4-bromobenzyl bromide (0.1 mmol). The reaction mixture was shaken for 1 hour, and the polymer-supported quenching reagent (100 mg) and DMF (0.5 mL) were added. The reaction mixture was shaken for 2 hours. Filtration, concentration, and partition between water and EtOAc gave the purified product. Note that in this instance, the polymer-supported quenching reagent both removes the excess 4-bromobenzyl bromide and cleaves the 2-nitrophenylsulfonyl protecting group.
MS(CI): 292, 290 (M+1).

EXAMPLE 23

Amide Synthesis From Amine and Carboxylic Acid

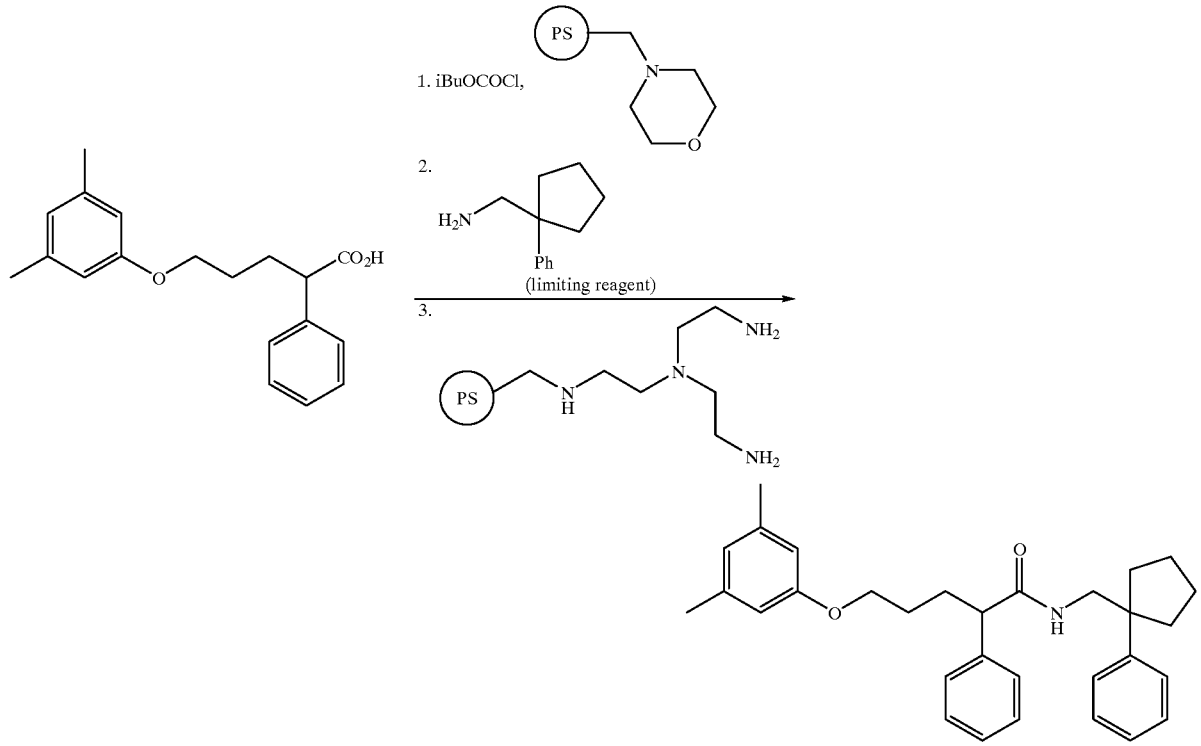

A mixture of the carboxylic acid (0.23 mmol), polymer-supported N-methylmorpholine (0.99 mmol), and DCM (2 mL) was treated with isobutyl chloroformate (0.23 mmol) and stirred at room temperature for 30 minutes before adding a solution of the amine (0.20 mmol) in DCM (1 mL). The reaction was stirred 2 hours, then the polymer-supported quenching reagent (100 mg) was added. The resulting slurry was stirred at room temperature for 3 hours, then filtered and solids rinsed with DCM. Combined filtrate and washings were evaporated to give amide product as an oil which crystallizes on standing. TLC on silica gel (CHCl3) shows one spot at Rf=0.3 upon staining with iodine vapor. MS(CI): 456 (M+1)

EXAMPLE 24
Hetero-Diels Alder Reaction

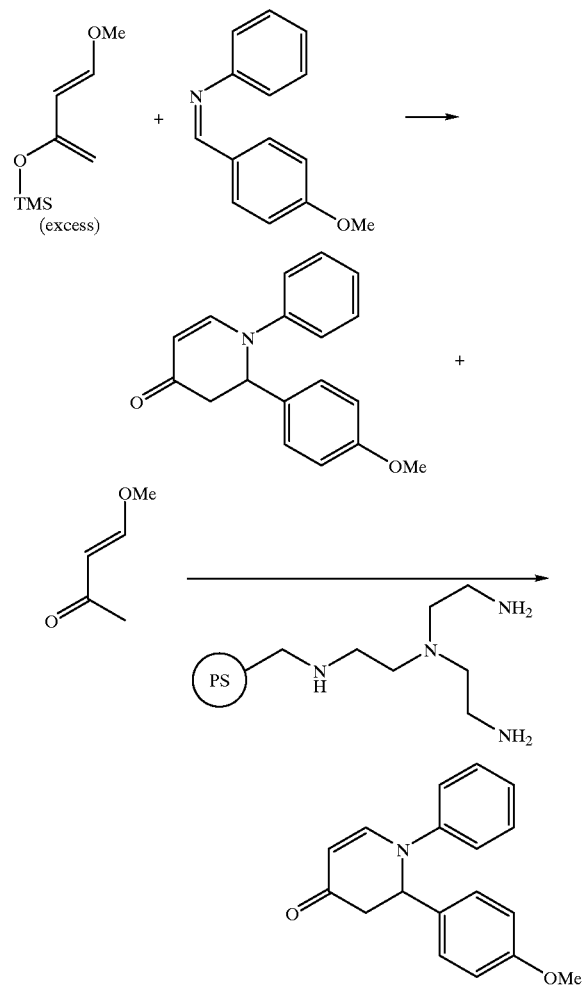

A solution of 4-methoxybenzylidene aniline (0.10 mmol), 1-methoxy-3-trimethylsilyloxy-1,3-butadiene (0.12 mmol), and Ytterbium(III)trifluoromethanesulfonate (0.01 mmol) in acetonitrile (1.2 mL) was stirred (room temperature, 30 minutes). The amine resin from Example 1 (100 mg) was added, and the resulting slurry was stirred (room temperature, 2 hours). The resulting slurry was filtered and the filtrate concentrated. The residue was partitioned between EtOAc and 1N HCl. The organic layer was washed with brine, dried (MgSO$_4$), and concentrated to give the purified dihydropyridone.

$^1$H NMR (CDCl$_3$): δ7.58 (d, J=8 Hz, 1H), 7.27–6.75 (m, 9H), 5.21 (d, J=8 Hz, 1H), 5.17 (dd, J=4 and 7 Hz, 1H), 3.71 (s, 3H), 3.19(dd, J=7 and 16 Hz, 1H), 2.69 (dd, J=4 and 16 Hz, 1H).

EXAMPLE 25
Suzuki Coupling

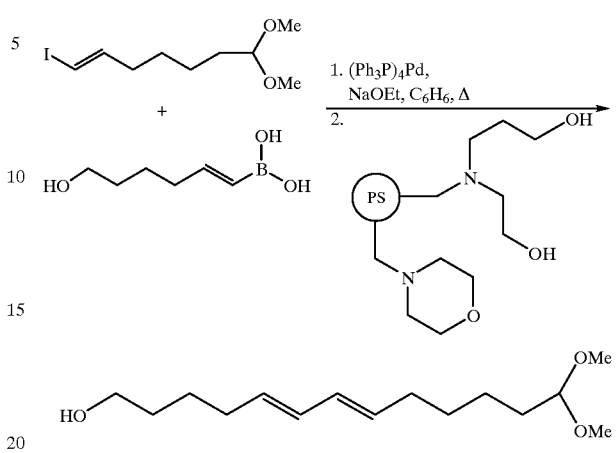

A solution of the iodide (0.23 mmol) and the vinylboronic acid (0.28 mmol) in 1.5 mL of freshly distilled benzene is treated under argon atmosphere with freshly prepared, degassed NaOEt (~1M, 0.68 mmol) in EtOH. Tetrakis (triphenylphosphine) palladium (13 mg, 0.01 mmol) is added, and the reaction is heated at reflux for 3 hours. The black mixture is cooled to room temperature, treated with the aminodiol resin from Example 10 (200 mg), and agitated for 2 hours. Et$_2$O-hexane (1:1, 4 mL) and silica gel (200 mg) are added, and the reaction mixture is filtered, rinsing the solids with Et$_2$O-hexane (1:1, 4 mL). The filtrate is evaporated to give the purified diene as an oil.

EXAMPLE 26
Two Component Condensation—Pyrazole Synthesis

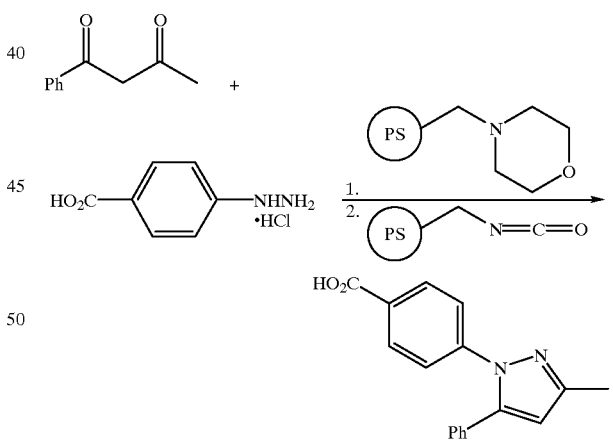

A suspension of polymer-supported morpholine (Example 12), 1-phenyl-1,3-butanedione (81.5 mg, 0.5 mmol) and 4-carboxyphenyl hydrazine hydrochloride (113 mg, 0.6 mmol) in MeOH (2 mL) was shaken for 2.5 hours. The methanol was blown off under a stream of N$_2$. DCM (4 mL) and polymer-supported isocyanate (Example 4A, 350 mg) were added and the reaction mixture shaken for 16 hours. An additional portion of polymer-supported isocyanate (120 mg) was added. After 4 hours the resin was filtered and washed with DCM (2×1.5 mL). The combined organic phases, when concentrated to dryness, gave 4-(3-methyl-5- phenyl-pyrazol-1-yl)-benzoic acid (67 mg, 48%), mp 159–162° C. Predicted mass for $(C_{17}H_{14}N_2O_2+H)^+$, 278.1055.
Found by HRMS (CI): 278.1055.

EXAMPLE 27
Three Component Condensation—Thiazolidinone Synthesis

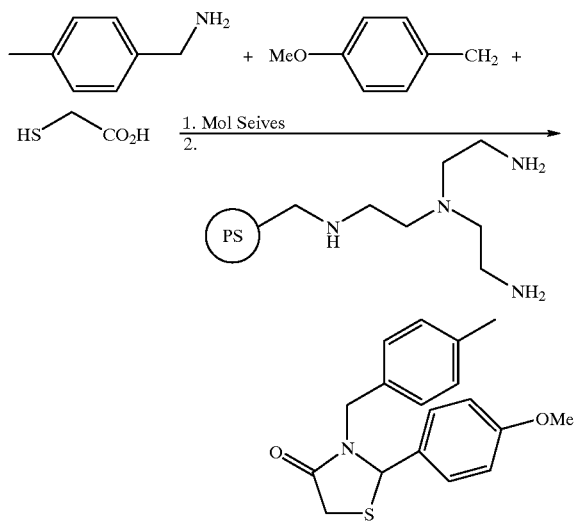

A mixture of 4-methylbenzylamine (0.10 mmol), 4-methoxybenzaldehyde (0.11 mmol), thioglycolic acid (0.25 mmol), toluene (5 mL), and 2A molecular seives (0.1 g) was heated to 100° C. for 1 hour. After cooling to room temperature, quenching amine resin (Example 1, 100 mg) and basic alumina (100 mg) were added. The resulting slurry was shaken 2 hours at room temperature. The solids w ere removed by filtration, rinsing with DCM. Solvent was blown off with a stream of warm air to afford 1-((4-methylphenyl)methyl)-2-(4-methoxyphenyl)-thiazolidinone.
MS(CI): 301 (M+1).

EXAMPLE 28
Thioether by S-alkylation

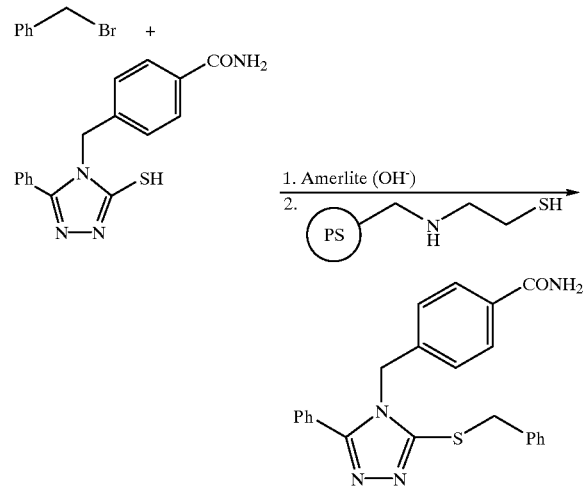

A solution of 4-((4-carboxamidophenyl)methyl)-5-phenyl-3-mercapto-1,2,4-triazole (0.1 mmol) in THF (6 mL) was treated with Amberlite resin ($OH^-$ form, 0.1 mmol $OH^-$) and benzyl bromide (0.15 mmol). The resulting mixture was shaken at room temperature until TLC showed that the starting thiol was consumed. Amino thiol resin (Example 13, 100 mg) was added and the mixture was shaken at room temperature for 1 hour. TLC showed that the excess benzyl bromide was consumed. The solids were removed by filtration and washed with DCM. Combined filtrates were evaporated to afford 4-((4-carboxamidophenyl)methyl)-5-phenyl-3-(phenylmethyl)thiol,2,4-triazole.

EXAMPLE 29

Two Component Condensation-2-(4-Iodophenyl)-[1,2,4]triazolo[2,3-d]pyridine Synthesis

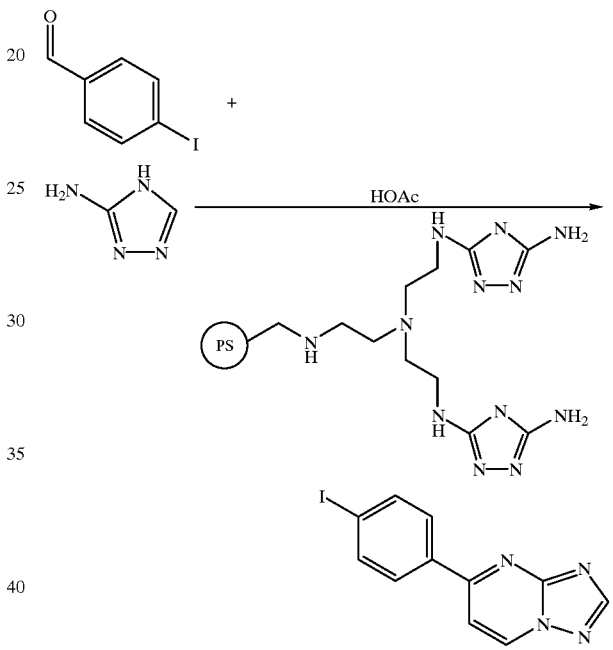

3-amino-1,2,4-triazole (88 mg, 1 mmol) and 1-dimethylamino-3-iodophenyl-1-propen-3-one (450 mg, 1.5 mmol) were refluxed in acetic acid (5 mL) for half an hour. The aminotriazole resin (from Example 17, 1 mmol) was added and the mixture refluxed for a further hour. The resin was filtered and the acetic acid removed under vacuum. A proton NMR shows pure 2-(4-iodophenyl)[1,2,4]triazolo[[2,3-d]pyridine.

MS(CI): 323 (M+1).
What is claimed is:
1. A solid compound P-L-Q wherein

P is comprised of poly(styrene-divinylbenzene);

Q is selected from the group consisting of $NHCH_2CH_2N(CH_2CH_2NH_2)_2$, $O(CH_2)_3CHO$, O-(3-formylpheny), $NHC(=S)NH_2NHCH_2CH_2SH$, 1-thiomorpholine, and 1-maleimide; and L is a group between P and Q selected from the group consisting of $CH_2-N$, $-CH_2-$ and $CH_2-CH_2-$.

2. A compound according to claim 1 wherein the polymer is a polymer that is insoluble in aqueous and organic solvents.

3. A compound according to claim 1 wherein the polymer is polystyrene copolymerized with less than 5% divinylbenzene.

4. A compound according to claim 1 wherein the Q functionality is present at a loading of at least 1 mmol per gram of polymer.

5. A compound according to claim 1 wherein the Q functionality is present at a loading of at least 2 mmol per gram of polymer.

6. A compound according to claim 1 of the structure

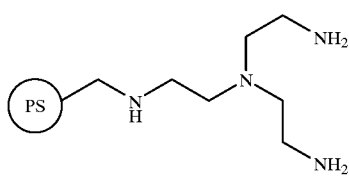

wherein

is polystyrene that is crosslinked with less than 5% divinylbenzene.

7. A compound according to claim 1 of the structure

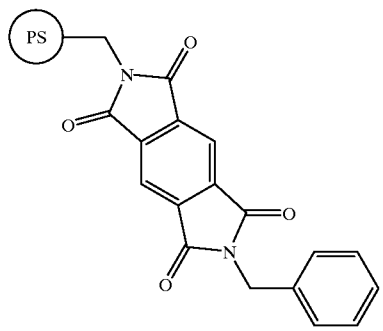

wherein

is polystyrene that is crosslinked with less than 5% divinylbenzene.

8. A compound according to claim 1 of the structure

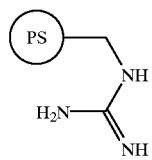

wherein

is polystyrene that is crosslinked with less than 5% divinylbenzene.

9. A compound according to claim 1 of the structure

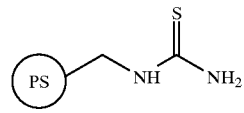

wherein

is polystyrene that is crosslinked with less than 5% divinylbenzene.

10. A compound according to claim 1 of the structure

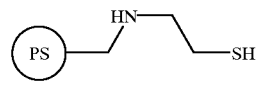

wherein

is polystyrene that is crosslinked with less than 5% divinylbenzene.

11. A compound according to claim 1 of the structure

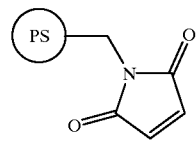

wherein

is polystyrene that is crosslinked with less than 5% divinylbenzene.

12. A compound according to claim 1 of the structure
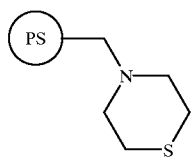
wherein
is polystyrene that is crosslinked with less than 5% divinylbenzene.
13. A compound according to claim 1 of the structure
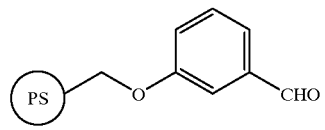
wherein
is polystyrene that is crosslinked with less than 5% divinylbenzene.
* * * * *

UNITED STATES PATENT AND TRADEMARK OFFICE
CERTIFICATE OF CORRECTION

PATENT NO. : 6,306,959 B1  
DATED : October 23, 2001  
INVENTOR(S) : Bolton, Gary L. et al.

It is certified that error appears in the above-identified patent and that said Letters Patent is hereby corrected as shown below:

Column 66,
Line 63, replace with -- NHC(=S)NH$_2$,-NHCH$_2$CH$_2$SH,1-thiomorpholine, and --.

Signed and Sealed this

First Day of July, 2003

JAMES E. ROGAN  
*Director of the United States Patent and Trademark Office*